(12) United States Patent
Vitari et al.

(10) Patent No.: US 9,968,688 B2
(45) Date of Patent: May 15, 2018

(54) SHIELDED TARGETING AGENTS, METHODS, AND IN VIVO DIAGNOSTIC SYSTEM

(71) Applicant: Verily Life Sciences LLC, Mountain View, CA (US)

(72) Inventors: Alberto Clemente Vitari, San Francisco, CA (US); Joshua Simon Klein, Mountain View, CA (US); Jerrod Joseph Schwartz, San Francisco, CA (US); Andrew Homyk, Belmont, CA (US); Marija Pavlovic, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 564 days.

(21) Appl. No.: 14/539,415

(22) Filed: Nov. 12, 2014

(65) Prior Publication Data

US 2016/0129131 A1   May 12, 2016

(51) Int. Cl.
    *A61B 5/05*   (2006.01)
    *A61K 47/48*   (2006.01)
    (Continued)

(52) U.S. Cl.
    CPC ...... *A61K 47/48884* (2013.01); *A61B 5/0071* (2013.01); *A61B 5/0515* (2013.01);
    (Continued)

(58) Field of Classification Search
    None
    See application file for complete search history.

(56) References Cited

U.S. PATENT DOCUMENTS 8,128,908 B2   3/2012   Santra et al.
8,246,968 B2   8/2012   Zale et al.
(Continued)

FOREIGN PATENT DOCUMENTS

CH   705 383 B1   2/2013
EP   2644192 A1   10/2013
(Continued)

OTHER PUBLICATIONS

"PCT International Search Report and Written Opinion", International Searching Authority, dated Jun. 2, 2016, pp. 1-21.
(Continued)

*Primary Examiner* — Joel F Brutus
(74) *Attorney, Agent, or Firm* — McDonnell Boehnen Hulbert & Berghoff LLP

(57) ABSTRACT

A system is provided which includes nanoparticle conjugates configured to bind with a tumor cell, the nanoparticle conjugate comprising a nanoparticle, at least one targeting entity bound to the nanoparticle, and at least one shielding entity that shields at the at least one targeting entity, the nanoparticle, or both; a body-mountable device mounted on an external surface of a living body and configured to detect a tumor cell binding response signal transmitted through the external surface, wherein the tumor cell binding response signal is related to binding of the nanoparticle conjugates with one or more tumor cells; and a processor configured to non-invasively detect the one or more tumor cells based on the tumor cell response signal. Nanoparticle conjugates and methods for use for treating or imaging tumor cells are also provided.

28 Claims, 21 Drawing Sheets

(51) Int. Cl.
- A61K 49/00 (2006.01)
- A61K 47/30 (2006.01)
- A61M 5/00 (2006.01)
- A61B 5/00 (2006.01)
- G01R 33/56 (2006.01)
- A61B 5/145 (2006.01)
- A61K 49/18 (2006.01)
- A61K 51/12 (2006.01)
- A61B 8/08 (2006.01)
- A61B 6/00 (2006.01)

(52) U.S. Cl.
CPC .......... *A61B 5/14546* (2013.01); *A61B 5/681* (2013.01); *A61K 47/30* (2013.01); *A61K 47/4823* (2013.01); *A61K 47/48238* (2013.01); *A61K 47/48569* (2013.01); *A61K 49/0002* (2013.01); *A61K 49/0004* (2013.01); *A61K 49/1824* (2013.01); *A61K 51/1244* (2013.01); *A61M 5/007* (2013.01); *G01R 33/5601* (2013.01); *A61B 6/481* (2013.01); *A61B 8/481* (2013.01)

(56) References Cited

U.S. PATENT DOCUMENTS

| | | | |
|---|---|---|---|
| 8,361,437 B2 | 1/2013 | Sharma et al. | |
| 2009/0155272 A1* | 6/2009 | Muschler | C07K 16/005 514/1.1 |
| 2009/0169478 A1 | 7/2009 | Leuschner et al. | |
| 2010/0034735 A1 | 2/2010 | Chen et al. | |
| 2010/0055099 A1* | 3/2010 | Filvaroff | C12Q 1/6809 424/133.1 |
| 2010/0183504 A1 | 7/2010 | Chen | |
| 2010/0260686 A1 | 10/2010 | Zhang et al. | |
| 2011/0268804 A1* | 11/2011 | Shi | A61K 39/00 424/489 |
| 2012/0035458 A1 | 2/2012 | Flynn | |
| 2012/0190975 A1 | 7/2012 | Chen et al. | |
| 2012/0213706 A1 | 8/2012 | Banerjee et al. | |
| 2013/0052131 A1 | 2/2013 | Zhen Chen et al. | |
| 2013/0197295 A1 | 8/2013 | Krishnan et al. | |
| 2014/0248210 A1 | 9/2014 | Bradbury et al. | |
| 2014/0286954 A1* | 9/2014 | Moe | C12Q 1/37 424/139.1 |

FOREIGN PATENT DOCUMENTS

| | | |
|---|---|---|
| WO | 2005/034926 A2 | 4/2005 |
| WO | 2009/089543 A2 | 7/2009 |
| WO | 2009091597 A2 | 7/2009 |
| WO | 2010120329 A1 | 10/2010 |
| WO | 2013173693 A1 | 11/2013 |
| WO | 2014145242 A1 | 9/2014 |

OTHER PUBLICATIONS

Blanco, et al., "Targeted Nanoparticles for Cancer Therapy," Recent Advances in Novel Drug Carrier Systems, 2012, Chapter 9, pp. 242-278.
Wei, et al., "Brain tumor-targeted drug delivery strategies," Acta Pharmaceutica Sinica B, 2014, vol. 4(3), pp. 193-201.
Avvakumova, et al., "Biotechnological approaches toward nanoparticle biofunctionalization," Trends in Biotechnology, Jan. 2014, vol. 32, No. 1, pp. 11-20.
Swami, et al., "Nanoparticles for Targeted and Temporally Controlled Drug Delivery," Multifunctional Nanoparticles for Drug Delivery Applications, Springer US, 2012, pp. 9-29.
Adolphi, et al., "Imaging of Her2-targeted magnetic nanoparticles for breast cancer detection: comparison of Squid-detected magnetic relaxometry and MRI," Contrast Media Mol. Imaging, 2012, vol. 7, pp. 308-319.
Poon, et al., "Layer-by-Layer Nanoparticles with a pH Sheddable layer for in Vivo Targeting of Tumor Hypoxia," ACS Nano, 2011 Jun. 28, vol. 5(6), pp. 4284-4292.
Meng, et al., "pH-Sensitive Polymeric Nanoparticles for Tumor-Targeting Doxorubicin Delivery: Concept and Recent Advances," Nanomedicine, 2014, vol. 9(3), pp. 487-499.
Shroff, et al., "Polymer Nanoparticles: Newer Strategies towards Targeted Cancer Therapy," J. Phys. Chem. Biophys., 2013, vol. 3(4), pp. 1-3.
Grover, et al., A Structurally Distinct Human Mycoplasma Protein that Generically Blocks Antigen-Antibody Union. Science, Feb. 7, 2014, vol. 343, pp. 656-661.
Dreaden, et al., "Bimodal Tumor-Targeting from Microenvironment Responsive Hyaluronan Layer-by-Layer (LbL) Nanoparticles," ACS Nano, 2014, vol. 8, No. 8, pp. 8374-8382.
Kwong et al., "Mass-encoded synthetic biomarkers for multiplexed urinary monitoring of disease," Nature Biotechnology, Jan. 2013, vol. 31, No. 1, pp. 63-70.
Armitage, Emily G., et al., "Metabolomics in Cancer Biomarker Discover: Current Trends and Future Perspectives", Journal of Pharmaceutical and Biomedical Analysis, vol. 87, Jan. 18, 2014, pp. 1-11. (Abstract only).
Hoffman, Allan S., et al., "Design of "Smart" Polymers that can Direct Intracellular Drug Delivery", Jan. 6, 2003, doi:10.1002/pat. 232. (Abstract only).
Liong, Monty, et al., "Multifunctional Inorganic Nanoparticles for Imaging, Targeting, and Drug Delivery", ACS Nano., May 2008, vol. 2(5), pp. 889-896, doi:10.1021/nn800072t.
McCarthy, Jason R., et al., "Multifunctional Magnetic Nanoparticles for Targeted Imaging and Therapy", Adv Drug Deily Rev., Aug. 17, 2008, vol. 60(11), pp. 1241-1251, doi:10.1016/j.addr. 2008.03.014.
Reddy, G.R., et al., "Vascular Targeted Nanoparticles for Imaging and Treatment of Brain Tumors", Clinical Cancer Research, Nov. 15, 2006, vol. 12(6677), pp. 1-23, doi:10.1158/1078-0432.CCR-06-0946.
Smith, Leon, et al., "Nanoparticles in Cancer Imaging and Therapy", Journal of Nanomaterials, 2012, vol. 2012, pp. 1-7, doi:10.1155/2012/891318.
Sounni, N.E., et al., "Targeting the Tumor Microenvironment for Cancer Therapy", Clin Chem, Nov. 28, 2012,7 vol. 59 (1), pp. 85-93, doi: 10.1373/clinchem.2012.185363. (Abstract only).
Sun, Conroy, et al., "Magnetic Nanoparticles in MR Imaging and Drug Deliver", Adv Drug Deliv Rev, Aug. 17, 2008, vol. 60(11), pp. 1252-1265, doi:10.1016/j.addr.2008.03.018.
Tsai, Ming-Ju, et al., "Tumor Microenvironment: A New Treatment Target for Cancer", ISRN Biochemistry, Apr. 13, 2014, vol. 2014, pp. 1-8, http://dx.doi.org/10.1155/2014/351959.
Yang, Ming, et al., "Oncometabolites: Linking Altered Metabolism with Cancer", J. Clin Invest., Sep. 3, 2013, vol. 123(9), pp. 3652-3658, doi:10.1172/JC167228.
Yu, Mi Kyung, et al., "Targeting Strategies for Multifunctional Nanoparticles in Cancer Imaging and Therapy", Theranostics, Jan. 1, 2012, vol. 2(1), pp. 3-44.
"Tumor Microenvironment", Wikipedia, pp. 1-9. [Retrieved from the Internet Nov. 7, 2014:<URL:http://en.wikipedia.org/wiki/Tumor_microenvironment>].
"About Imaging Agents or Tracers", American College of Radiology Imaging Network. [Retrieved from the Internet Nov. 10, 2014:<URL:http://www.acrin.org/patients/aboutimagingexamsandagents/aboutimagingagentsortracers.aspx>].
Aaron, J.S., et al., "Increased Optical Contrast in Imaging of Epidermal Growth Factor Receptor Using Magnetically Actuated Hybrid Gold/Iron Oxide Nanoparticles", Optics Express, Dec. 25, 2006, vol. 14(26), pp. 12930-12943.
Li, J., et al., "Enzyme-Responsive Cell-Penetrating Peptide Conjugated Mesoporous Silica Quantum Dot Nanocarriers For Controlled Release of Nucleus-Targeted Drug Molecules and Real-Time Intracellular Fluorescence Imaging of Tumor Cells", Advanced Healthcare Materials, 2014, vol. 3(8), pp. 1230-1239, doi:10.1002/adhm.201300613.

(56) References Cited

OTHER PUBLICATIONS

Liu, Y., et al., "Multifunctional pH-Sensitive Polymeric Nanoparticles for Theranostics Evaluated Experimentally in Cancer", Nanoscale, 2014, vol. 6(6), pp. 3231-3242, doi:10.1039/c3nr05647c.

Vivek, R., et al., "Multifunctional HER2-Antibody Conjugated Polymeric Nanocarrier-Based Drug Delivery System for Multi-Drug-Resistant Breast Cancer Therapy", ACS Applied Materials & Interfaces, 2014, vol. 6(9), pp. 6469-6480, dx.doi.org/10.1021/am406012g.

Zhang, J., et al., "Multifunctional Envelope-Type Mesoporous Silica Nanoparticles for Tumor-Triggered Targeting Drug Deiivery", J. Am. Chem. Soc., 2013, vol. 135(13), pp. 5068-5073, dx.doi.org/10.1021/ja312004m.

International Bureau, International Preliminary Report on Patentability dated May 26, 2017, issued in connection with International Application No. PCT/US2015/060092, filed on Nov. 11, 2015, 13 pages.

\* cited by examiner

SHIELDED TARGETING AGENTS, METHODS, AND IN VIVO DIAGNOSTIC SYSTEM

BACKGROUND

Unless otherwise indicated herein, the materials described in this section are not prior art to the claims in this application and are not admitted to be prior art by inclusion in this section.

The tumor microenvironment is the cellular environment in which the tumor exists, including surrounding blood vessels, immune cells, fibroblasts, other cells, signaling molecules, and the extracellular matrix. The tumor and the surrounding microenvironment are closely related and interact constantly. Tumors can influence the microenvironment by releasing extracellular signals, promoting tumor angiogenesis and inducing peripheral immune tolerance, while the immune cells in the microenvironment can affect the growth and evolution of cancerous cells, such as in immune-editing. The tumor microenvironment has also been shown to contribute to tumor heterogeneity. Because of the importance of the tumor microenvironment in supporting cancer growth and development, the tumor microenvironment has become a target for cancer drug development.

Much effort has been devoted into developing nanoparticles as vehicles for tumor detection, imaging and diagnosis as well as for the treatment of cancer. The nanoparticle-based therapies and imaging applications can be targeted to selectively extravasate through tumor vasculature via the enhanced permeation and retention (EPR) effect. Nanoparticles have been conjugated to drugs, imaging agents, or other substances that can be delivered to specific sites either by active targeting or by size-dependent passive targeting. However, one challenge associated with use of nanoparticles in vivo is the specific delivery of nanoparticles to tumor cells. Many tumor biomarkers are also expressed on normal tissue which may result in toxicity or negatively impact the pharmacokinetics of tumor antigen-specific nanoparticles resulting from the unintended targeting of nanoparticles to normal tissue. Furthermore, nanoparticles can be deactivated or destroyed by the body before they reach their target. Accordingly, there is a need for improved nanoparticle conjugates that are shielded from degradation and/or deactivation by the body and that exploits the tumor microenvironment for targeted delivery of imaging and/or therapeutic agents to tumor cells for use in imaging, diagnostic and/or therapeutic methods to determine the medical condition of a patient and for treating cancer.

SUMMARY

Some embodiments of the present disclosure provide a shielded nanoparticle conjugate comprising: (a) a nanoparticle; (b) at least one targeting entity bound to the nanoparticle and configured to bind to tumor cells or tissue; and (c) at least one shielding entity that shields the at least one targeting entity, the nanoparticle, or both.

Some embodiments of the present disclosure also provide a method for in vivo imaging in a mammal of tumor cells or tissue that express a selected marker including the steps of: (a) administering to the mammal a shielded nanoparticle conjugate comprising: (i) a nanoparticle; (ii) at least one targeting entity bound to the nanoparticle and configured to bind to tumor cells or tissue; and (iii) at least one shielding entity that shields the at least one targeting entity, the nanoparticle, or both, wherein the targeting entity is specific for the selected marker; (b) waiting a time sufficient to allow the targeting entity to bind to the selected markers of the tumor cells or tissue; and (c) imaging the cells or tissue with a non-invasive imaging technique that has a resolution enhanced by the presence of the conjugate on or within the cells or tissue.

Some embodiments of the present disclosure further provide a method for inhibiting the growth of tumor cells or tissue in a mammal, said method including: (a) administering an effective amount of a shielded nanoparticle conjugate comprising: (i) a nanoparticle; (ii) at least one targeting entity bound to the nanoparticle and configured to bind to tumor cells or tissue; and (iii) at least one shielding entity that shields the at least one targeting entity, the nanoparticle, or both, wherein the targeting entity is specific for the selected marker, to said mammal, wherein the targeting entity is specific for a marker that is specifically expressed by the tumor cells or tissue.

Another embodiment of the present disclosure provide a system including: (a) plurality of nanoparticle conjugates, each nanoparticle conjugate comprising a nanoparticle, at least one targeting entity bound to the nanoparticle and configured to bind with a tumor cell, and at least one shielding entity that shields at the at least one targeting entity, the nanoparticle, or both (b) body-mountable device, wherein the body-mountable device is mountable on an external surface of a living body and configured to detect a tumor cell binding response signal transmitted through the external surface of the living body, wherein the tumor cell binding response signal is related to binding of the nanoparticle conjugates with one or more tumor cells; and (c) a processor configured to non-invasively detect the one or more tumor cells based on the tumor cell response signal. The device can include a detector to detect the analyte response signal.

A further embodiment of the present disclosure provides a method including: (a) introducing a plurality of nanoparticle conjugates into an environment, each nanoparticle conjugate comprising a nanoparticle, at least one targeting entity bound to the nanoparticle and configured to bind with a tumor cell or tissue, and at least one shielding entity configured to shield the nanoparticle, the at least one targeting entity, or both; (b) detecting a response signal transmitted from the environment, wherein the response signal includes a tumor cell response signal that is related to binding of the nanoparticle conjugates to tumor cells and wherein the response signal is modulated; and (c) detecting one or more tumor cells by differentiating the response signal from a background signal, at least in part, based on the modulation.

These as well as other aspects, advantages, and alternatives, will become apparent to those of ordinary skill in the art by reading the following detailed description, with reference where appropriate to the accompanying drawings.

DETAILED DESCRIPTION

Figure 1:
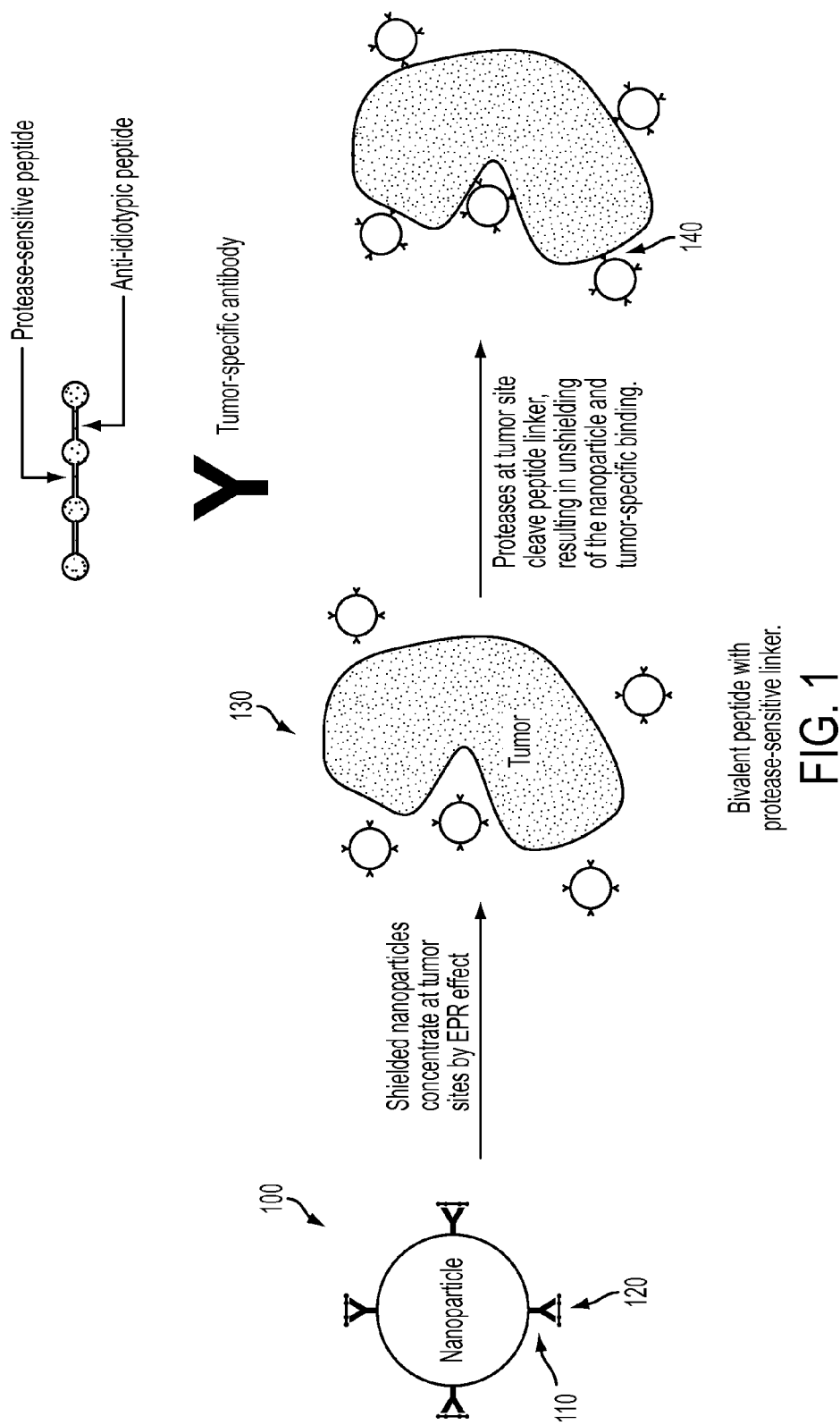
FIG. 1 illustrates the interaction of a shielded nanoparticle conjugate with a tumor cell involving protease-catalyzed deshielding of a shielding entity in the tumor cell microenvironment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Nanoparticle Conjugate Overview

One of the most important factors contributing to a positive prognosis of cancer is early detection. Unfortunately, identification of tumors during early stages, before they have reached substantial sizes or metastasized, is often extremely difficult due to their inaccessibility, particularly for cancers which reside deep within the body. For such deep tumors, biopsies or other surgical procedures are too invasive for routine diagnosis. Traditional optical imaging techniques suffer from shallow penetration due to the significant scattering and absorption of the surrounding tissue. While many alternative techniques undergo substantially less scattering and are therefore capable of achieving sufficient depth, such as ultrasonic imaging, magnetic resonance imaging (MRI), positron emission tomography (PET), and x-ray imaging, the lack of scattering implies poor contrast between different media, imposing similarly severe challenges to tumor imaging.

To overcome these challenges, labeled agents are often employed to provide sufficient contrast for deep imaging modalities. In such usage, the images essentially correspond to the density of the contrast agent, rather than the specific tissue of interest. For these images to accurately reflect a particular entity in the body, these agents must be designed to selectively bind to the specific target of interest. In the case of tumor imaging, such targeting is often achieved through the use of antibodies or aptamers which bind to surface proteins expressed by the cancer cells. Additionally, achieving specific binding to tumor cells could aid in the delivery of therapeutic compounds for treatment. Ideally, completely specific binding would also allow reduced dosages of both imaging and therapeutic agents, reducing the potential hazard to healthy tissue. Unfortunately, many of these characteristics are shared with healthy tissue, degrading the specificity of the targeting as the labeled agents become trapped at the wrong locations. Not only does this require higher dosages to compensate, the excess tag concentration presents a background signal which degrades image quality and can pose hazards to normal tissue function.

In the present disclosure, shielded nanoparticle targeting agents or probes which employ multiple layers have been specially designed to prevent unintended binding to a wrong target before arrival at the tumor. Upon initial delivery to circulation, the targeting entity, for example an antibody or aptamer, would be hidden or shielded underneath a protective layer and unavailable for binding. After reaching the tumor location, release of the shielding layer, e.g., deshielding or unshielding, by the tumor microenvironment would expose the binding agent, thereby enabling specific binding at the tumor location. This deshielding process could be triggered by another factor which is specific to the tumor such as low pH or metabolite. Unlike the case of conventional labeled agents, the activation of the shielding layer can be triggered by the tumor environment itself, and does not rely on achieving long-term binding to the cell surface. This enables a much broader variety of triggering mechanisms, for example by using pH-specific polymers which release in the tumor environment or protease-cleavage of bivalent peptides as discussed herein. In addition to improving the binding specificity, these shields would also protect the nanoparticle during transport to the tumor site, further improving delivery efficiency. The highly precise delivery of contrast agents and therapeutics to tumor sites will greatly improve our ability to detect, image and treat cancer.

II. Illustrative Nanoparticle Conjugates

Nanoparticles have been widely used as catalysts, photocatalysts, adsorbents, and sensors. More recently, nanoparticles have been used for the diagnosis and treatment of diseases. Nanoparticles can bind or be linked to natural or synthetic substances such as drugs, medicaments, diagnostic agents, antisense oligonucleotides, proteins, plasmids etc. and carry such substances to target organs in the human or animal body, such as the brain, liver, kidneys and other organs. In particular, nanoparticles have been used for the treatment of cancers. Nanoparticles conjugated to drugs can be delivered to specific sites by either active targeting or by size-dependent passive targeting (Cancer Res. 1986; 46:6387-6392; J. Control. Release 1999; 62:253-262).

Active drug targeting is a method of selectively delivering anticancer elements to cancer cells by conjugating nanoparticles containing anticancer agents to recognition or targeting groups that bind or react with cancer cells. Nanoparticles-based drugs designed in this manner allow for controlled local release of drugs at specific drug targets defined by the recognition groups. Prime examples of active targeting method are lectin and carbohydrate, ligand and acceptor, or antibody and antigen (Farhan J. Ahmad, et al., Nanotechnology: A Revolution in the Making, The Pharma Review December 2005).

Passive drug targeting, on the other hand, employs enhanced permeation and retention (EPR) effect to specifically target cancer cells. The EPR effect is a phenomenon that is is commonly found only in cancer cells and in angiogenic vascular structures of cancer. The EPR effect in cancer cells is characterized by non-selective absorption, permeation, and retention of macromolecules having a macromolecule size between 10 to 200 nm, usually around 100 to 200 nm.

While nanoparticle conjugates are of interest for tumor diagnosis and therapeutic drug delivery, one challenge associated with nanoparticle use in vivo is the specific delivery of nanoparticles to tumor cells. The unintended targeting of nanoparticles to normal tissue may limit the application of nanoparticles for diagnostic or therapeutic applications. Coating of nanoparticles with antibody, small molecules, or aptamers targeting tumor biomarkers, e.g., ERBB2, FOLR1, EGFR, FOLH1) can improve specific delivery of nanoparticles. However, many of these biomarkers are expressed abundantly on normal tissues, which may result in toxicity or negatively impact the pharmacokinetics of the antigen-specific nanoparticle. Thus, many tumor-specific biomarkers are expressed by other healthy cells and tissues, thereby limiting their use in the development of targeting agents for cancer diagnosis and treatment. Accordingly, there is a need for improved functionalized nanoparticles that are selectively targeted to tumor cells.

In one aspect, the present disclosure provides a nanoparticle conjugate having a shielding or cloaking functionality that can protect the nanoparticle, including any agents carried by the nanoparticle, from degradation or deactivation by body. Once at the tumor microenvironment, the nanoparticle (including an agent to be delivered if present) can be deshielded and the nanoparticle can bind to the tumor cell and/or undergo cellular uptake. The advantages of shielding the nanoparticle in such a manner include: pre-labeling of tumor tissue enables the detection of extravasating cells that leave the tumor and enter circulation which can be readily detected by a wearable device; minimization of losses in the active concentration of the targeted nanoparticle by off-target binding; lower dosage amounts and increased therapeutic benefit for a given nanoparticle dosage; minimization of toxicity due to off-target binding; and increased contrast and reduced false-positive rates for tumor detection.

In one embodiment, a shielded nanoparticle conjugate is provided. The shielded nanoparticle comprises: (i) a nanoparticle; (ii) at least one targeting entity bound to the nanoparticle and configured to bind to tumor cells or tissue; and (iii) at least one shielding entity that shields the at least one targeting entity, the nanoparticle, or both. In some embodiments, the nanoparticle comprises a polymer or non-polymer material. In other embodiments, the nanoparticle comprises magnetic or paramagnetic material.

In one embodiment, the targeting entity comprises an antibody, peptide, protein, nucleic acid, small molecule, carbohydrate, or lipid.

In another embodiment, the shielding entity is a pH-sensitive polymer, an idiopathic aptamer directed to a tumor metabolite, or a protease-sensitive bivalent peptide. In some embodiments, the targeting entity is an antibody and the shielding entity is a protease-sensitive bivalent peptide that binds to the antigen binding site of the antibody. In other embodiments, the targeting entity is an antibody and the shielding entity is a pH-sensitive polymer that degrades in an acidic tumor microenvironment. In further embodiments, the targeting entity is an antibody and the shielding entity is a bivalent anti-idiotypic aptamer with a tumor metabolite-binding domain, wherein the aptamer binds to the antigen binding site of the antibody.

In one embodiment, the nanoparticle conjugate can be a therapeutic or diagnostic agent. In some embodiments, the nanoparticle conjugate can further include at least one detection label. In other embodiments, the nanoparticle conjugate can further include at least one agent to be delivered to the tumor cells. In some embodiments, the agent can be at least one anti-tumor agent. In other embodiments, the agent can be a contrast imaging agent.

In another embodiment, the nanoparticle conjugate can include at least one moiety that exhibits fluorescence, magnetic or paramagnetic properties, or both.

a. Nanoparticles

The term "nanoparticle" refers to any particle having a diameter of less than 1000 nanometers (nm). In some embodiments, nanoparticles can be optically or magnetically detectable. In some embodiments, intrinsically fluorescent or luminescent nanoparticles, nanoparticles that comprise fluorescent or luminescent moieties, plasmon resonant nanoparticles, and magnetic nanoparticles are among the detectable nanoparticles that are used in various embodiments. In general, the nanoparticles should have dimensions small enough to allow their uptake by eukaryotic cells. Typically the nanoparticles have a longest straight dimension (e.g., diameter) of 200 nm or less. In some embodiments, the nanoparticles have a diameter of 100 nm or less. Smaller nanoparticles, e.g. having diameters of 50 nm or less, e.g., 5 nm-30 nm, are used in some embodiments.

In some embodiments, nanoparticles under 400 nm, typically between 100 nm and 200 nm, may be characterized by enhanced accumulation in tumors. While not wishing to be bound by any theory, enhanced accumulation in tumors may be caused by the increased permeability of angiogenic tumor vasculature relative to normal vasculature. Nanoparticles can diffuse through such "leaky" vasculature, resulting in accumulation of nanoparticles in tumors.

In one embodiment, nanoparticles are quantum dots, i.e., bright, fluorescent nanocrystals with physical dimensions small enough such that the effect of quantum confinement gives rise to unique optical and electronic properties. In certain embodiments, optically detectable nanoparticles are metal nanoparticles. Metals of use in the nanoparticles include, but are not limited to, gold, silver, iron, cobalt, zinc, cadmium, nickel, gadolinium, chromium, copper, manganese, palladium, tin, and alloys and/or oxides thereof. In some embodiments, magnetic nanoparticles are of use in accordance with the invention. "Magnetic nanoparticles" refers to magnetically responsive nanoparticles that contain one or more metals or oxides or hydroxides thereof.

In other embodiments, the nanoparticles are made from polymers or lipids See for instance, EP 2644 192; U.S. Pat. No. 8,246,968; U.S. patent publication no. 2013/0037977; U.S. Pat. No. 5,478,860; U.S. Patent Publ. no. 2004/0142025; International patent publication nos. WO 01/05373, 2014/057432, and 2014/037498; and EP 2698066, which are incorporated by reference in their entirety.

In other embodiments, the nanoparticle comprises a bulk material that is not intrinsically fluorescent, luminescent, plasmon resonant, or magnetic. The nanoparticle comprises one or more fluorescent, luminescent, or magnetic moieties. For example, the nanoparticle may comprise QDs, fluorescent or luminescent organic molecules, or smaller nanoparticles of a magnetic material. In other embodiments, the nanoparticles are made from polymers.

In some embodiments, a nanoparticle composed in part or in whole of an organic polymer is used. A wide variety of organic polymers and methods for forming nanoparticles therefrom are known in the art. For example, nanoparticles composed at least in part of polymethylmethacrylate, polyacrylamide, poly(vinyl chloride), carboxylated poly(vinyl chloride), or poly(vinyl chloride-co-vinyl acetate-co-vinyl alcohol) may be used. Optionally the nanoparticle comprises one or more plasticizers or additives. Co-polymers, block co-polymers, and/or grafted co-polymers can be used.

In some embodiments, the nanoparticles can be labeled with fluorescent and luminescent moieties include a variety of different organic or inorganic small molecules commonly referred to as "dyes," "labels," or "indicators." Examples include fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g. Valeur, B., "Molecular Fluorescence: Principles and Applications," John Wiley and Sons, 2002; Handbook of Fluorescent Probes and Research Products, Molecular Probes, 9th edition, 2002; and The Handbook-A Guide to Fluorescent Probes and Labeling Technologies, Invitrogen, $10^{th}$ edition).

In some embodiments, the nanoparticles are biocompatible and/or biodegradable. As used herein, the term "biocompatible" refers to substances that are not toxic to cells. In some embodiments, a substance is considered to be "biocompatible" if its addition to cells in vivo does not induce inflammation and/or other adverse effects in vivo. In some embodiments, a substance is considered to be "biocompatible" if its addition to cells in vitro or in vivo results in less than or equal to about 50%, about 45%, about 40%, about 35%, about 30%, about 25%, about 20%, about 15%, about 10%, about 5%, or less than about 5% cell death. In general, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

In some embodiments, a nanoparticle which is biocompatible and/or biodegradable may be associated with a targeting entity and/or an agent to be delivered that is not biocompatible, is not biodegradable, or is neither biocompatible nor biodegradable. In some embodiments, a nanoparticle which is biocompatible and/or biodegradable may be associated with a shielding entity and/or an agent to be delivered is also biocompatible and/or biodegradable.

Nanoparticles can have a coating layer. Use of a biocompatible coating layer can be advantageous, e.g., if the nanoparticles contain materials that are toxic to cells. Suitable coating materials include, but are not limited to, natural proteins such as bovine serum albumin (BSA), biocompatible hydrophilic polymers such as polyethylene glycol (PEG) or a PEG derivative, phospholipid-(PEG), silica, lipids, polymers, carbohydrates such as dextran, and other nanoparticles, etc. Coatings may be applied or assembled in a variety of ways such as by dipping, using a layer-by-layer technique, conjugation, etc.

In some embodiments, the nanoparticles may optionally comprise one or more dispersion media, surfactants, release-retarding ingredients, or other pharmaceutically acceptable excipient. In some embodiments, nanoparticles may optionally comprise one or more plasticizers or additives.

In some embodiments, nanoparticles may be intrinsically magnetic nanoparticles. In some embodiments, fluorescent or luminescent nanoparticles, nanoparticles that comprise fluorescent or luminescent moieties, and plasmon resonant nanoparticles can be useful. In some embodiments, the nanoparticles have detectable optical and/or magnetic properties. An optically detectable nanoparticle is one that can be detected within a living cell using optical means compatible with cell viability. Optical detection is accomplished by detecting the scattering, emission, and/or absorption of light that falls within the optical region of the spectrum, i.e., that portion of the spectrum extending from approximately 180 nm to several microns. Optionally a sample containing cells is exposed to a source of electromagnetic energy. In some embodiments, absorption of electromagnetic energy (e.g. light of a given wavelength) by the nanoparticle or a component thereof is followed by the emission of light at longer wavelengths, and the emitted light is detected. In some embodiments, scattering of light by the nanoparticles is detected. In certain embodiments, light falling within the visible portion of the electromagnetic spectrum, i.e., the portion of the spectrum that is detectable by the human eye (approximately 400 nm to approximately 700 nm) is detected. In some embodiments, light that falls within the infrared or ultraviolet region of the spectrum is detected.

The optical property can be a feature of an absorption, emission, or scattering spectrum or a change in a feature of an absorption, emission, or scattering spectrum. The optical property can be a visually detectable feature such as, for example, color, apparent size, or visibility (i.e. simply whether or not the particle is visible under particular conditions). Features of a spectrum include, for example, peak wavelength or frequency (wavelength or frequency at which maximum emission, scattering intensity, extinction, absorption, etc. occurs), peak magnitude (e.g., peak emission value, peak scattering intensity, peak absorbance value, etc.), peak width at half height, or metrics derived from any of the foregoing such as ratio of peak magnitude to peak width. Certain spectra may contain multiple peaks, of which one is typically the major peak and has significantly greater intensity than the others. Each spectral peak has associated features. Typically, for any particular spectrum, spectral features such as peak wavelength or frequency, peak magnitude, peak width at half height, etc., are determined with reference to the major peak. The features of each peak, number of peaks, separation between peaks, etc., can be considered to be features of the spectrum as a whole. The foregoing features can be measured as a function of the direction of polarization of light illuminating the nanoparticles; thus polarization dependence can be measured. Features associated with hyper-Rayleigh scattering can be measured. Fluorescence detection can include detection of fluorescence modes. Luminescence detection can also be useful for optical imaging purposes.

In various embodiments, intrinsically fluorescent or luminescent nanoparticles, nanoparticles that comprise fluorescent or luminescent moieties, plasmon resonant nanoparticles, and magnetic nanoparticles are among the detectable nanoparticles that can be used. Such nanoparticles can have a variety of different shapes including variety of different shapes including spheres, oblate spheroids, cylinders, ovals, ellipses, shells, cubes, cuboids, cones, pyramids, rods (e.g., cylinders or elongated structures having a square or rectangular cross-section), tetrapods (nanoparticles having four leg-like appendages), triangles, prisms, etc. Nanoparticles can be also solid or hollow and can comprise one or more layers (e.g., nanoshells, nanorings, etc.). Nanoparticles may have a core/shell structure, wherein the core(s) and shell(s) can be made of different materials. Nanoparticles may comprise gradient or homogeneous alloys. Nanoparticles may be composite nanoparticles made of two or more materials, of which one, more than one, or all of the materials possess magnetic properties, electrically detectable properties, and/or optically detectable properties.

In general, the nanoparticles should have dimensions small enough to allow their uptake by eukaryotic cells. Typically the nanoparticles have a longest straight dimension (e.g., diameter) of 200 nm or less. In some embodiments, the nanoparticles have a diameter of 100 nm or less. Smaller nanoparticles, e.g. having diameters of 50 nm or less, e.g., 5 nm-30 nm, are used in some embodiments in accordance with the invention.

The targeting entity and/or imaging agents and/or therapeutic agents can be attached to the nanoparticles via a linking agent. The agents and nanoparticle can be conjugated via a single linking agent or multiple linking agents. For example, the imaging agent and nanoparticle may be conjugated via a single multifunctional (e.g., bi-, tri-, or tetra-) linking agent or a pair of complementary linking agents. In another embodiment, the targeting agent and the nanoparticle are conjugated via two, three, or more linking agents. Suitable linking agents include, but are not limited to, e.g., functional groups, affinity agents, stabilizing groups, and combinations thereof.

In certain embodiments the linking agent is or comprises a functional group. Functional groups include monofunctional linkers comprising a reactive group as well as multifunctional crosslinkers comprising two or more reactive groups capable of forming a bond with two or more different functional targets (e.g., labels, proteins, macromolecules, semiconductor nanocrystals, or substrate). In some preferred embodiments, the multifunctional crosslinkers are heterobifunctional crosslinkers comprising two or more different reactive groups.

Suitable reactive groups include, but are not limited to thiol (—SH), carboxylate (COOH), carboxyl (—COOH), carbonyl, amine ($NH_2$), hydroxyl (—OH), aldehyde (—CHO), alcohol (ROH), ketone ($R_2CO$), active hydrogen, ester, sulfhydryl (SH), phosphate (—$PO_3$), or photoreactive moieties. Amine reactive groups include, but are not limited to e.g., isothiocyanates, isocyanates, acyl azides, NHS esters, sulfonyl chlorides, aldehydes and glyoxals, epoxides and oxiranes, carbonates, arylating agents, imidoesters, carbodiimides, and anhydrides. Thiol-reactive groups include, but are not limited to e.g., haloacetyl and alkyl halide derivates, maleimides, aziridines, acryloyl derivatives, arylating agents, and thiol-disulfides exchange reagents. Carboxylate reactive groups include, but are not limited to e.g., diazoalkanes and diazoacetyl compounds, such as carbonyldiimidazoles and carbodiimides. Hydroxyl reactive groups include, but are not limited to e.g., epoxides and oxiranes, carbonyldiimidazole, oxidation with periodate, N,N'-disuccinimidyl carbonate or N-hydroxylsuccimidyl chloroformate, enzymatic oxidation, alkyl halogens, and isocyanates. Aldehyde and ketone reactive groups include, but are not limited to e.g., hydrazine derivatives for schiff base formation or reduction amination. Active hydrogen reactive groups include, but are not limited to e.g., diazonium derivatives for mannich condensation and iodination reactions. Photoreactive groups include, but are not limited to e.g., aryl azides and halogenated aryl azides, benzophenones, diazo compounds, and diazirine derivatives.

Other suitable reactive groups and classes of reactions useful in practicing the present invention include those that are well known in the art of bioconjugate chemistry. Currently favored classes of reactions available with reactive chelates are those which proceed under relatively mild conditions. These include, but are not limited to, nucleophilic substitutions (e.g., reactions of amines and alcohols with acyl halides, active esters), electrophilic substitutions (e.g., enamine reactions), and additions to carbon-carbon and carbon-heteroatom multiple bonds (e.g., Michael reaction, Diels-Alder addition). These and other useful reactions are discussed in, for example, March (1985) Advanced Organic Chemistry, 3rd Ed., John Wiley & Sons, New York, Hermanson (1996) Bioconjugate Techniques, Academic Press, San Diego; and Feeney et al. (1982) Modification of Proteins; Advances in Chemistry Series, Vol. 198, American Chemical Society, Washington, D.C., which are incorporated by reference in their entirety.

In some embodiments, the linking agent is a chelator. For example, the chelator comprising the molecule, DOTA (DOTA=1,4,7,10-tetrakis(carboxymethyl)-1,4,7,10-tetraazacyclododecane), that can readily be labeled with a radiolabel, such as $Gd^{3+}$ and $^{64}Cu$, resulting in $Gd^{3-}$-DOTA and $^{64}Cu$-DOTA respectively, attached to the quantum dot (nanoparticle). Optical properties of the cores (luminescence or fluorescence emission or plasmon frequency) are not affected by the addition of a silica shell or the presence of chelated paramagnetic ions. Other suitable chelates are known to those of skill in the art, for example, 1,4,7-triazacyclononane-N,N',N''-triacetic acid (NOTA) derivatives being among the most well-known (see, e.g., Lee et al. (1997) Nucl Med Biol. 24:225-23019).

In some, embodiments the linking agent is a heterobifunctional crosslinker comprising two different reactive groups that form a heterocyclic ring that can interact with a peptide. For example, a heterobifunctional crosslinker such as cysteine may comprise an amine reactive group and a thiol-reactive group can interact with an aldehyde on a derivatized peptide. Additional combinations of reactive groups suitable for heterobifunctional crosslinkers include, for example, amine- and sulfhydryl reactive groups; carbonyl and sulfhydryl reactive groups; amine and photoreactive groups; sulfhydryl and photoreactive groups; carbonyl and photoreactive groups; carboxylate and photoreactive groups; and arginine and photoreactive groups. In some embodiments, an affinity agent (e.g., agents that specifically binds to a ligand) is the linking agent. In these embodiments, a first linking agent is bound to the semiconductor nanocrystal (nanoparticle) and a second linking agent is bound to the imaging, targeting or therapeutic agent. Affinity agents include receptor-ligand pairs, antibody-antigen pairs and other binding partners such as streptavidin/avidin and biotin. In one illustrative embodiment, the first linking agent is streptavidin or avidin and the second linking agent is biotin. the streptavidin or avidin is bound to the nanoparticle and a biotinylated agent (e.g., biotinylated imaging agent, biotinylated therapeutic, biotinylated antibody, etc.) is conjugated to the nanoparticle via streptavidin/avidin-biotin linkage. In some embodiments, other biotinylated radiolabel, peptides, proteins, antibodies, dyes, probes and other small molecules are attached to the streptavidin or avidin, and thus the nanoparticle.

b. Targeting Entity

In one embodiment, the nanoparticle is associated with one or more targeting entities. In general, a "targeting entity" is any entity that binds to a component (also referred to as a "target" or a "marker") associated with an organ, tissue, cell, subcellular locale, and/or extracellular matrix component. A targeting entity may be a nucleic acid (e.g., aptamer), polypeptide, glycoprotein, carbohydrate, lipid, etc. For example, a targeting entity can be a nucleic acid targeting entity (e.g. an aptamer) that binds to a cell type specific marker. In general, an aptamer is an oligonucleotide (e.g., DNA, RNA, or an analog or derivative thereof) that binds to a particular target, such as a polypeptide. In some embodiments, a targeting entity may be a naturally occurring or synthetic ligand for a cell surface receptor, e.g., a growth factor, hormone, LDL, transferrin, etc. A targeting entity can be an antibody, which term is intended to include antibody fragments, characteristic portions of antibodies, single chain antibodies, etc. Synthetic binding proteins such as affibodies, etc., can be used. Peptide targeting entities can be identified, e.g., using procedures such as phage display. This widely used technique has been used to identify cell specific ligands for a variety of different cell types.

In some embodiments, targeting entities bind to an organ, tissue, cell, extracellular matrix component, and/or intracellular compartment that is associated with a specific developmental stage or a specific disease state (i.e. a "target" or "marker"). In some embodiments, a target is an antigen on the surface of a cell, such as a cell surface receptor, an integrin, a transmembrane protein, an ion channel, and/or a membrane transport protein. In some embodiments, a target is an intracellular protein. In some embodiments, a target is a soluble protein, such as immunoglobulin. In some embodiments, a target is more prevalent, accessible, and/or abundant in a diseased locale (e.g. organ, tissue, cell, subcellular locale, and/or extracellular matrix component) than in a healthy locale. In some embodiments, a target is preferentially expressed in tumor tissues versus normal tissues. In some embodiments, a target is more prevalent, accessible, and/or abundant in locales (e.g. organs, tissues, cells, subcellular locales, and/or extracellular matrix components) associated with a particular developmental state than in locales associated with a different developmental state. In some embodiments, targeting entities facilitate the passive entry into target sites by extending circulation time of conjugates, reducing non-specific clearance of conjugates, and/or geometrically enhancing the accumulation of conjugates in target sites.

As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which structure is used, e.g., physiological conditions. In some embodiments, the moieties are attached to one another by one or more covalent bonds. In some embodiments, the moieties are attached to one another by a mechanism that involves specific (but non-covalent) binding (e.g. streptavidin/avidin interactions, antibody/antigen interactions, etc.). In some embodiments, a sufficient number of weaker interactions can provide sufficient stability for moieties to remain physically associated.

In one embodiment, the targeting agent is an antibody. As used herein, the term "antibody" refers to any immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. Such proteins may be derived from natural sources, or partly or wholly synthetically produced. An antibody may be monoclonal or polyclonal. An antibody may be a member of any immunoglobulin class, including any of the human classes: IgG, IgM, IgA, IgD, and IgE. As used herein, the terms "antibody fragment" refers to any derivative of an antibody which is less than full-length. In general, an antibody fragment retains at least a significant portion of the full-length antibody's specific binding ability. Examples of antibody fragments include, but are not limited to, Fab, Fab', F(ab')2, scFv, Fv, dsFv diabody, and Fd fragments. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains which are linked together, for example, by disulfide linkages. An antibody fragment may optionally comprise a multimolecular complex. A functional antibody fragment typically comprises at least about 50 amino acids and more typically comprises at least about 200 amino acids.

Antibodies to these and other cancer markers are known to those of skill in the art and can be obtained commercially or readily produced by known methods such as using phage-display technology.

In one embodiment, the targeting entity binds to a marker, e.g., tumor marker, on a tumor cell. As used herein, the terms "tumor cells," "cancer cells," "carcinomas," and "tumor tissue" are used interchangeably and are inclusive of all such cell types known in the art, including but not limited to fibrosarcoma, myxosarcoma, lip osarcoma, chondrosarcoma, osteogenic sarcoma, chordoma, angiosarcoma, endotheliosarcoma, lymphangiosarcoma, lymphangioendothetiosarcoma, synovioma, mesothelioma, Ewing's tumor cells, leiomyosarcoma, rhabdomyosarcoma, colon carcinoma, pancreatic cancer cells, breast cancer cells, ovarian cancer cells, prostate cancer cells, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor cells, cervical cancer cells, testicular tumor cells, lung carcinoma, small cell lung carcinoma, bladder carcinoma, epithelial carcinoma, glioma, astrocytoma, medulloblastoma, craniopharyngioma, ependymoma, pinealoma, hemangio-blastoma, acoustic neuroma, oligodendroglioma, meningioma, melanoma, neuroblastoma, retinoblastoma; leukemias, e.g., acute lymphocytic leukemia and acute myelocytic leukemia (myeloblasts, promyelocytic, myelomonocytic, monocytic and erythroleukemia.

A large number of cancer markers are known to those of skill in the art. Some cell surface components of cancer cells are common to normal cells and others are either qualitatively distinct for or quantitatively increased in tumor cells. Cell surface components common to both normal and malignant cells include, e.g., various kinds of receptors (e.g., certain hormone receptors), histocompatibility antigens, blood group antigens, and differentiation antigens. Receptors include, e.g., sheep erythrocyte receptor, hormone receptors, e.g., estrogen receptor and the like, transferrin receptor, Fc immunoglobulin receptor, nerve growth factor receptor, and the like. Blood group antigens include, e.g., the P determinant and M and N precursor ("T antigen"). Examples of differentiation antigens include surface immunoglobulin, and onco-neural antigens. Examples of histocompatibility antigens include HLA-A, HLA-B, HLA-DR (Ia-like). In cases where the cell-surface antigen is qualitatively distinct for cancer cells or quantitatively increased in cancer as compared to non-cancer tissues such cell surface markers will be useful as targets for localizing antibodies.

The term "cancer markers" (used interchangeably with "marker" and "tumor marker") refers to biomolecules such as proteins that are useful in the diagnosis and prognosis of cancer. As used herein, "cancer markers" include but are not limited to: PSA, human chorionic gonadotropin, alpha-fetoprotein, carcinoembryonic antigen, cancer antigen (CA) 125, CA 15-3, CD20, CDH13, CD 31, CD34, CD105, CD146, D16S422HER-2, phospatidylinositol 3-kinase (PI 3-kinase), trypsin, trypsin-1 complexed with alpha(1)-antitrypsin, estrogen receptor, progesterone receptor, c-erbB-2, be 1-2, S-phase fraction (SPF), p185erbB-2, low-affinity insulin like growth factor-binding protein, urinary tissue factor, vascular endothelial growth factor, epidermal growth factor, epidermal growth factor receptor, apoptosis proteins (p53, Ki67), factor VIII, adhesion proteins (CD-44, sialyl-TN, blood group A, bacterial lacZ, human placental alkaline phosphatase (ALP), alpha-difluoromethylornithine (DFMO), thymidine phosphorylase (dTHdPase), thrombomodulin, laminin receptor, fibronectin, anticyclins, anti-cyclin A, B, or E, proliferation associated nuclear antigen, lectin UEA-1, cea, 16, and von Willebrand's factor. In some embodiments, certain molecules such as metabolites are produced in excess or reduced quantities in tumor cells relative to normal tissue and these metabolites can also serve as a tumor marker. Representative examples of tumor metabolites produced at excessive levels include lactate in solid tumors; D-2-hydroxyglutarate in IDH1 or IDH2 mutant cancers; fumarate in fumarate hydratase mutant cancers; and succinate in succinate dehydrogenase mutant cancers. Reduced levels of oxygen and glucose have been found in solid tumors. For a discussion of oncometabolites, see for instance, Yang, M., Soga, T., & Pollard, P. J. (2013) and Journal of Clinical Investigation, 123(9), 3652-3658. doi:10.1172/JCI67228.

Cancer markers also include tumor-specific antigens. Antigens that are more restricted to tumor cells include, e.g., inappropriately (ectopically) expressed normal antigens, modified normal antigens, and neoantigens, such as embryonic and fetal antigens, viral antigens, and tumor-specific (or tumor-associated) antigens. Examples of embryonic and fetal antigens include fetal onco-neural antigens, onco-fetal antigens, melanoma antigens, colorectal cancer antigens, lung cancer antigens, breast cancer antigens and the like. An example of a virus-associated antigen is the viral capsid antigen of Epstein-Barr virus.

Tumor-specific antigens, by the strictest definition, are not present on normal cells during any stage of development or differentiation. These may result from mutation of structural genes, abnormal gene transcription or translation, abnormal post-translational modification of proteins, derepression of normally repressed genes, or insertion of genes from other cells or organisms ("transfection"). Since only about 1000 gene products have been identified for the approximately 1 million genes in mammalian cells, new tumor-associated antigens will probably be previously undefined normal gene products. An antigen need not be tumor-specific in the strictest sense to be useful as a target marker for localizing antibodies used for detection or therapy. For example, an inappropriate receptor may serve as a selective target for antibodies used for cancer detection or therapy. Examples of tumor-specific or tumor-associated antigens include CEA, melanoma cell surface antigens, breast cancer cell surface antigens, lung cancer cell surface antigens, colorectal cancer cell surface antigens, gastric cancer cell surface antigens, pancreatic cancer cell surface antigens, glioma cell surface antigens, common sarcoma cell surface antigens, gastrointestinal cancer cell surface antigens, brain tumor cell surface antigens, esophageal cancer cell surface antigens, common epithelial cancer cell surface antigens, osteosarcoma cell surface antigens, fibrosarcoma cell surface antigens, urinary bladder cancer cell surface antigens, prostatic cancer cell surface antigens, renal cancer cell surface antigens, ovarian cancer cell surface antigens, testicular cancer cell surface antigens, endometrial cancer cell surface antigens, cervical cancer cell surface antigens, Hodgkin's disease cell surface antigens, lymphoma cell surface antigens, leukemic cell surface antigens, trophoblastic tumor cell surface antigens, and the like.

c. Shielding Entity

In certain embodiments, nanoparticles and/or agents are associated with one or more components that protect the nanoparticle and/or agent to be delivered; these components are referred to as a "shielding entity". The shielding entity protects the nanoparticle and/or agent while in transit and/or controls the delivery or activity of the nanoparticle to prevent degradation and increase circulation life-time of the nanoparticle until the nanoparticle reaches the tumor site (e.g., tumor cell or tissue) where the nanoparticle is subsequently deshielded by the tumor microenvironment.

i. Protease-Cleavable Bivalent Peptides

Proteases such as matrix metalloproteases (MMPs) are generally highly expressed in many types of tumors. Therefore, nanoparticles which include shielding protease sensitive substrates having a protease-cleavable bond can be released when the nanoparticles reach tumor sites in vivo, allowing the nanoparticle to bind to the tumor site. In one embodiment, nanoparticles labeled with antibodies bound to shielding bivalent-peptides sensitive to tumor protease and its use in a method for targeting a tumor site is provided. By screening peptide libraries to identify a peptide that binds to the antigen binding site of an antibody with weak affinity, two copies of the protease-sensitive peptide can be linked together with an anti-idiopathic peptide to create a high affinity bivalent-peptide shield with increased avidity to the antigen binding site of the antibody. Exemplary peptide sequences and proteases that target these sequences can be found in Funovics et al., 2003, Anal. Bioanal. Chem., 377:956; and Harris et al., 2006, Angew. Chem. Int. Ed., 45:3161, both of which are incorporated herein by reference in their entirety. Although the bivalent peptide acts as shield to block binding of the nanoparticles to the antigen, the bivalent peptide includes a protease cleavage site that is selectively recognized by certain proteases in tumor tissues such as cathepsin B, FOLH1, MMP2 and MMP9 and is cleaved in tumor tissues. The weak affinity of the now monomeric peptide results in the rapid unshielding of the antigen binding site in the tumor microenvironment, thus enabling tumor biomarker-specific delivery of the nanoparticle. Without the protease, the bivalent peptide remains attached to the antibody. Thus, cleavage and deshielding can occur at tumor sites where corresponding proteases are present.

As shown in FIG. 1, shielded nanoparticle 100 labeled with antibodies 110 bound to the protease-sensitive bivalent peptide 120 is introduced into a patient where it concentrated at tumor sites, e.g., tumor 130, by the EPR effect. Proteases at the tumor site cleave the bivalent peptide linker 120, thus unshielding the nanoparticle and allowing for targeted tumor-specific binding 140.

ii. Environmentally Sensitive Polymer

Tumor tissue is characterized by an extracellular tumor microenvironment that is more acidic than the pH of the blood or other normal extracellular tissue microenvironments. In one embodiment, nanoparticles coated with an environmentally sensitive polymer such as a pH sensitive polymer which is sensitive to an acidic extracellular tumor microenvironment and its use in a method for targeting a tumor site is provided. By coating or layering a targeting molecule (e.g., antibody, small molecule, or aptamer) of a nanoparticle with a pH-sensitive polymer to form a shielded nanoparticle, the targeting molecule would be stabilized and shielded during transport in blood, for instance, and would undergo rapid degradation (e.g, by hydrolysis) once the nanoparticle is exposed to the relatively acidic (lower pH) tumor microenvironment, thereby enabling tumor biomarker-specific delivery of the nanoparticle. The targeting molecule itself can be designed or selected to have a low target affinity in neutral pH, and increased affinity at acidic pH. This can be accomplished by a variety of means including through a conformational change of the molecule (e.g., protein/aptamer refolding) or the alteration of the binding site properties (e.g., protonation of certain sites, overall ionic charge, or steric size).

Suitable protective pH-sensitive polymer include, but are not limited to, poly(L-histidine-co-phenylalanine)-poly(ethylene glycol) block copolymer, poly(L-lactic acid)-poly (ethylene glycol) block copolymer, poly(acrylic acid) polymers, poly(ethyl acrylic acid), poly(propyl acrylic acid), and poly(butyl acrylic acid). The pH-dependent activity of poly (acrylic acid) polymers could be employed in order to shield the nanoparticle targeting molecule. Systematic increases in the length of the alkyl group by one methylene unit ($CH_2$) have been shown to increase the polymer's pKa value which affects the pH at which the polymer undergoes a conformational change. For instance, pKa increases from 6.3 for poly(ethyl acrylic acid) to 6.7 for poly(propyl acrylic acid) and to 7.4 for poly(butyl acrylic acid). Other pH-sensitive polymeric materials include polyelectrolytes that have a large number of ionizable groups such as poly(sulfonic acid) polymers and their derivatives, hyaluronic acid, poly(vinylamine), and poly(N-isopropylacrylamide). See for instance, Hoffman, P S Stayton, O Press, N Murthy, et al., Design of "Smart" Polymers that can direct intracellular drug delivery, Polymers for Advanced Technologies 13 (2002) 992-999, which are incorporated by reference in its entirety.

The pH-sensitive polymer can be coated or layered onto the nanoparticle by any suitable means including spraying or dipping.

Figure 2:
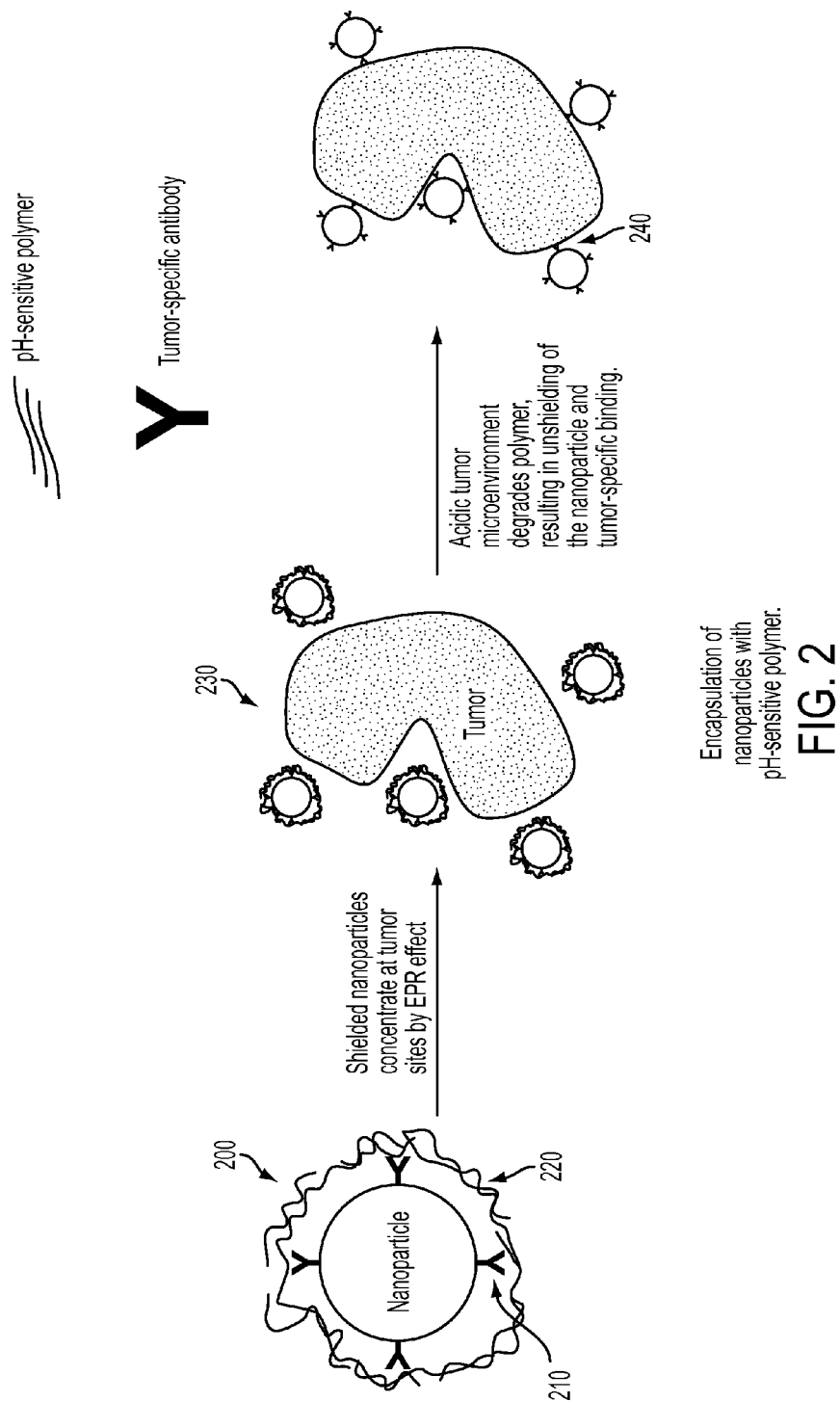
FIG. 2 illustrates the interaction of a shielded nanoparticle conjugate with a tumor cell involving low pH deshielding of a shielding entity in an acidic tumor cell microenvironment.

As shown in FIG. 2, shielded nanoparticle 200 labeled with tumor-specific antibodies 210 and coated with a pH-sensitive polymer 230 is introduced into a patient where it concentrated at tumor sites, e.g., tumor 220, by the EPR effect. The acidic tumor microenvironment degrades the polymer, resulting in the unshielding of the nanoparticle and allowing for tumor-specific binding of the nanoparticle 240.

iii. Bivalent Anti-Idiotypic Aptamer with Metabolite-Binding Domain

Many tumor markers are made by normal cells as well as by cancer cells; however, they are produced at much higher levels in cancerous conditions compared to blood and other normal tissue extracellular microenvironment. These substances can be found in the blood, urine, stool, tumor tissue, or other tissues or bodily fluids of some patients with cancer. More than 20 different tumor markers have been characterized and are in clinical use. Some are associated with only one type of cancer, whereas others are associated with two or more cancer types. While most tumor markers are proteins, metabolites such as lactate and D-2-hydroxyglutarate (D2HG) also serve as tumor markers as they are present at elevated levels in the tumor extracellular microenvironment.

In one embodiment, anti-idiotypic aptamers bound to a tumor specific antibody on a nanoparticle and its use in a method for targeting a tumor site is provided. Tumor tissue is characterized by an elevated lactate or D2HG compared to blood and other normal tissue extracellular microenvironment. In this embodiment, shielding of the tumor-targeting antibody is achieved by using an aptamer that has been selected to bind to the antigen binding site of the antibody in the absence of a high concentration of lactate but dissociates from the antibody in the present of lactate due to either direct competition for the binding site or allostery. Alternatively, reduced levels of a molecule (e.g., oxygen) in the tumor microenvironment could trigger the release of the nanoparticle shield. As defined herein, an anti-idiotypic aptamer is an aptamer that reacts with the individual structural determinants (idiotypes) on the variable region of an antibody. Commonly referred to as "synthetic antibodies," aptamers are pre-selected single-stranded oligonucleotide (e.g., DNA or RNA) or peptide molecules that bind to specific target molecules including proteins and peptides with affinities and specificities that are comparable to antibodies. Aptamers have a wide range of applications including diagnostics and therapeutics and can be chemically synthesized using known techniques.

Figure 3:
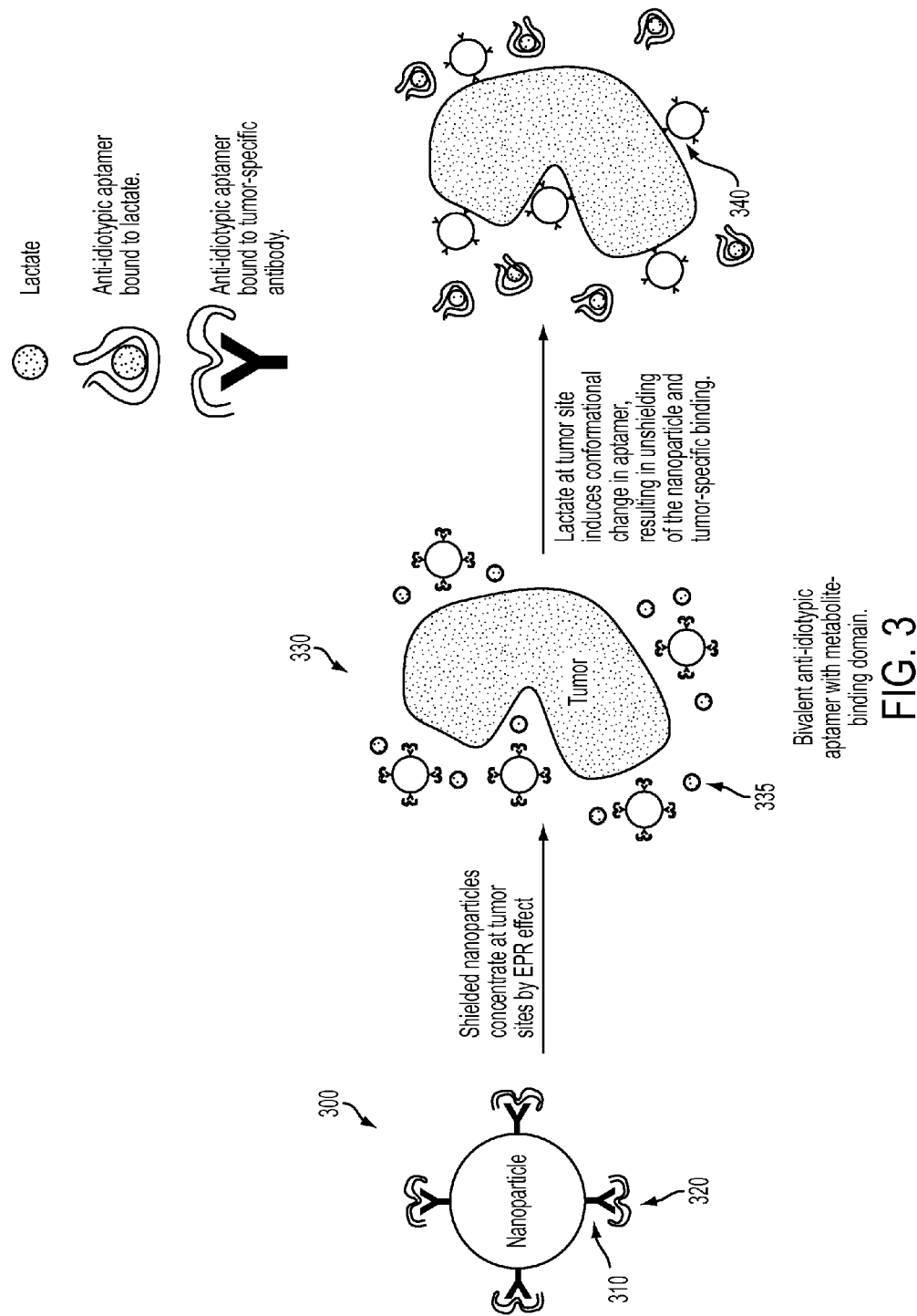
FIG. 3 illustrates the interaction of a shielded nanoparticle conjugate with a tumor cell involving displacement of a shielding entity by a tumor metabolite in the tumor cell microenvironment.

As shown in FIG. 3, shielded nanoparticle 300 labeled with tumor-specific antibodies 310 bound to an anti-idiopathic aptamer 320 is introduced into a patient where it concentrated at tumor sites, e.g., tumor 330, by the EPR effect. The presence of excessive amounts of tumor metabolite lactate 335 in the tumor microenvironment induces a conformational change in the aptamer, resulting in the unshielding of the nanoparticle and allowing for tumor-specific binding of the nanoparticle conjugate 340.

iv. Multi-Level Shielding

In some embodiments, nanoparticles are associated with one or more shielding entities as described above can serve to cloak the nanoparticle, targeting entities, and/or the agent and provide multi-level shielding. In one embodiment, a nanoparticle having a tumor specific antibody targeting entity is first shielded by protease sensitive bivalent-peptides and the shielded nanoparticle can be further shielded using an environmentally-sensitive polymer such as a low pH sensitive polymer. In other embodiments, a nanoparticle having a tumor-specific antibody targeting entity is first shielded by an anti-idiotypic aptamer and the shielded nanoparticle can be further shielded using an environmentally-sensitive polymer. In other embodiments, a nanoparticle can have a variety of tumor specific antibodies, one which is shielded by bivalent-peptides and others by anti-idiotypic aptamers. Reinforced specificity/redundancy can be particularly useful for delivery of therapeutics.

v. Two-Step Endogenous and/or Exogenous Triggering

In another embodiment, the use of an endogenous and/or exogenous triggering mechanism can further provide additional enhancement of specificity or prevent errant unshielding. For instance, treatment could involve an initial injection of a benign sensitizer, a delay for a period of time to allow for uptake by the tumor, and finally injection of the functionalized nanoparticles. In some embodiments, the sensitizer can be passively taken up by the tumor cells based on the EPR effect. In other embodiments, the sensitizer can include active targeting elements such as aptamers, antibodies, or small molecules. For instance, a sensitizer can be a pH-activated polymer and include a tumor specific antibody as a targeting agent. The functionalized nanoparticle can have a sensitizer-specific cleavage site such that neither the sensitizer nor the functionalized NP would have any effect but only in combination does the NP bind and activate.

III. Methods Using Shielded Nanoparticle Conjugates

In some embodiments, the shielded nanoparticle conjugates further includes at least one agent (e.g., payload) to be delivered to the tumor cell or tissue.

As used herein, the phrase "agent to be delivered" or "payload" refers to any substance that can be delivered to a tissue, cell, or subcellular locale. In some embodiments, the agent to be delivered is a biologically active agent, i.e., it has activity in a biological system and/or organism. For instance, a substance that, when administered to an organism, has a biological effect on that organism, is considered to be biologically active. In some embodiments, the agent to be delivered is a therapeutic, diagnostic, imaging and/or prophylactic agent. The therapeutic agents (e.g. anti-cancer agents), diagnostic agents (e.g. contrast agents; radionuclides; and fluorescent, luminescent, and magnetic moieties), prophylactic agents (e.g. vaccines), and/or nutraceutical agents (e.g. vitamins, minerals, etc.) may be delivered by the shielding nanoparticle conjugates. Exemplary agents include, but are not limited to, small molecules (e.g. cytotoxic agents), nucleic acids (e.g., siRNA, RNAi, and microRNA agents), proteins (e.g. antibodies), peptides, lipids, carbohydrates, hormones, metals, radioactive elements and compounds, drugs, vaccines, immunological agents, etc., and/or combinations thereof. In some embodiments, the agent to be delivered is an agent useful in the treatment of cancer (e.g., prostate or breast cancer).

In specific embodiments, the agent to be delivered is a therapeutic agent such as an anti-tumor drug. Representative anti-tumor drugs include, without limitation, doxorubicin, paclitaxel, adriamycin, cisplatin, 5-fluorouracil, mitomycin, chlomomycin, bleomycin, peplomycin, daunorubicin, aclarubicin, neocarzinostatin, epirubicin, idarubicin and pirarubicin.

In some embodiments, an agent to be delivered may function as a targeting entity as described herein. For instance, an antibody that is useful for targeting the nanoparticle conjugates to specific tissues may also serve as a therapeutic agent. In some embodiments, the agent to be delivered may be distinct from a targeting entity.

The nanoparticle conjugate compositions may be administered to a subject using any amount and any route of administration effective for imaging and/or treating a tumor or cancer. Representative examples include injection, ingestion, inhalation, transdermally, or in some other manner. The exact amount required will vary from subject to subject, depending on the species, age, and general condition of the subject, the severity of the disease, the particular composition, its mode of administration, its mode of activity and the like. Compositions in accordance with the invention are typically formulated in dosage unit form for ease of administration and uniformity of dosage.

It will be understood, however, that the total daily usage of the compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In one embodiment, the nanoparticle conjugate can include one or more additional agents that can further enhance cellular uptake of the nanoparticle conjugate by the tumor cell. These agents include, without limitation, transfection agents which alter the intracellular delivery of the nanoparticle and include cationic or neutral lipids; polysaccharides; translocation entities which is typically a peptide; and endosome disrupting or fusogenic entity such as fusogenic peptides.

a. Therapeutic Treatment Method

The shielded nanoparticle conjugates can be used to treat, alleviate, ameliorate, relieve, delay onset of, inhibit progression of, reduce severity of, and/or reduce incidence of one or more symptoms or features of a disease, disorder, and/or condition. For instance, the shielded nanoparticle conjugates can be used to treat cancer and/or cancer cells. In one embodiment, a method is provided for killing or inhibiting the growth of tumor cells or tissue in a mammal which comprising administering an effective amount of the nanoparticle conjugate to the mammal, wherein the targeting entity is specific for a marker that is specifically expressed by the tumor cells or tissue. In some embodiments, the method further includes a step of imaging the cells or tissue with a non-invasive imaging technique whose resolution is enhanced by the presence of the conjugate on or within the cells.

The term "cancer" includes pre-malignant as well as malignant cancers. Cancers include, but are not limited to, prostate, gastric cancer, colorectal cancer, skin cancer, e.g., melanomas or basal cell carcinomas, lung cancer, cancers of the head and neck, bronchus cancer, pancreatic cancer, urinary bladder cancer, brain or central nervous system cancer, peripheral nervous system cancer, esophageal cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. "Tumor cells" or "Cancer cells" as defined above, can be in the form of a tumor, exist alone within a subject (e.g., leukemia cells), or be cell lines derived from a cancer.

In one embodiment, the payload is a drug or a combination of more than one drug. Such nanoparticle conjugates may be useful, for example, in embodiments where a targeting entity may be used to direct a nanoparticle containing a drug to a particular localized location within a subject, e.g., to allow localized delivery of the drug to occur. Exemplary therapeutic agents include chemotherapeutic agents such as doxorubicin (adriamycin), gemcitabine (gemzar), daunorubicin, procarbazine, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-11, 10-hydroxy-7-ethyl-camptothecin (SN38), dacarbazine, S-I capecitabine, ftorafur, 5'deoxyfluorouridine, UFT, eniluracil, deoxycytidine, 5-azacyto sine, 5-azadeoxycyto sine, allopurinol, 2-chloroadeno sine, trimetrexate, aminopterin, methylene-10-deazaminopterin (MDAM), oxaplatin, picoplatin, tetraplatin, satraplatin, platinum-DACH, ormaplatin, CI-973, JM-216, and analogs thereof, epirubicin, etoposide phosphate, 9-aminocamptothecin, 10,11-methylenedioxycamptothecin, karenitecin, 9-nitrocamptothecin, TAS 103, vindesine, L-phenylalanine mustard, ifosphamidemefosphamide, perfosfamide, trophosphamide carmustine, semustine, epothilones A-E, tomudex, 6-mercaptopurine, 6-thioguanine, amsacrine, etoposide phosphate, karenitecin, acyclovir, valacyclovir, ganciclovir, amantadine, rimantadine, lamivudine, zidovudine, bevacizumab, trastuzumab, rituximab, 5-Fluorouracil, and combinations thereof.

In some embodiments, a method for the treatment of cancer is provided. In some embodiments, the treatment of cancer comprises administering a therapeutically effective amount of the shielded nanoparticle conjugates to a subject in need thereof, in such amounts and for such time as is necessary to achieve the desired result. In certain embodiments of the present invention a "therapeutically effective amount" of shielded nanoparticle conjugates is that amount effective for treating, alleviating, ameliorating, relieving, delaying onset of, inhibiting progression of, reducing severity of, and/or reducing incidence of one or more symptoms or features of cancer.

In some embodiments, shielded nanoparticle conjugates is administered to a subject in such amounts and for such time as is necessary to achieve the desired result (i.e. treatment of cancer). In certain embodiments of the present invention a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

In other embodiments, the nanoparticles of the present invention can be used to inhibit the growth of cancer cells, e.g., prostate cancer cells. As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging (MRI), computerized axial tomography and X-rays. Cancer cell growth can also be determined indirectly, such as by determining the levels of circulating carcinoembryonic antigen, prostate specific antigen or other cancer-specific antigens that are correlated with cancer cell growth Inhibition of cancer growth is also generally correlated with prolonged survival and/or increased health and well-being of the subject.

In one embodiment, the nanoparticles can comprise one or more therapeutic agents. In some embodiments, the therapeutic agent is conjugated to the nanoparticles. For instance, the therapeutic agent can be conjugated to an outer surface or a layer of the nanoparticle.

In some embodiments, the therapeutic agent comprises one or more agents selected from the group consisting of a photosensitizer, a radiosensitizer, an ESR heating moiety, an isotope, a cytotoxin, and a cancer drug. In particular embodiments the therapeutic agent comprises an isotope selected from the group consisting of $^{99}$Tc, $^{203}$Pb, $^{67}$Ga, $^{68}$Ga, $^{72}$As, $^{111}$In, $^{113}$In, $^{97}$Ru, $^{62}$Cu, $^{641}$Cu, $^{52}$Fe, $^{52}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{177}$Lu, $^{105}$Rh, and $^{111}$Ag. In certain embodiments the therapeutic moiety comprises an isotope that is a gamma emitter. In certain embodiments the therapeutic moiety comprises a photosensitizer selected from the group consisting of a haematoporphyrin derivative, photophrin II, a benzoporphyrins, a tetraphenyl porphyrin, a chlorine, and a phthalocyanine.

b. Imaging Method

In another embodiment of the invention, a method is provided for in vivo imaging in a mammal of tumor cells or tissue that express a selected marker. The method includes the steps of: (a) administering to the mammal a nanoparticle conjugate, wherein the targeting entity is specific for the selected marker; (b) waiting a time sufficient to allow the targeting entity to bind to the selected markers of the tumor cells or tissue; and (c) imaging the cells or tissue with a non-invasive imaging technique that has a resolution enhanced by the presence of the conjugate on or within the cells or tissue. The amount of time sufficient to allow the targeting entity to bind can vary from patient to patient as well as the type of tumor cells or tissue that is being imaged and the amount of nanoparticle conjugates being administered. In general, the amount of time can range for instance from 30 minutes to 24 hours, one hour to 12 hours, or one hour to three hours, In some embodiments, the imaging technique is selected from the group consisting of magnetic resonance imaging (MRI), magnetic spectroscopy, X-ray, positron emission tomography (PET), computer tomography (CT), photoacoustic imaging, and ultrasonic imaging.

Imaging techniques can non-invasively measure biological functions, evaluate cellular and molecular events, and reveal the inner workings of a body. Examples of imaging techniques include magnetic resonance imaging (MRI), positron emission tomography (PET), x-ray tomography, luminescence and fluorescence (optical imaging), deep tissue Near Infrared (NIR) imaging, ultrasound imaging, and photoacoustic imaging. Each of these techniques can differ from one another in the resolution, sensitivity, and anatomical information they provide about the subject. For example, though optical imaging has high sensitivity, it provides limited anatomical background information, and can display artifacts due to tissue absorbance and scattering. MRI can be used to generate contrast to detect tumors in deep tissue and provide true three dimensional imaging of biological structures and processes at cellular resolution. X-ray contrast is useful to differentiate tissues with small differences in their density.

In certain embodiments, shielded nanoparticle conjugates are provided that are useful as imaging (e.g., contrast) agents, and/or therapeutics. In various embodiments the nanoparticle conjugates are effective a multiple-modality effectors. That is, they can simultaneously provide one or more imaging modalities, and/or one or more targeting modalities, and/or one or more therapeutic modalities.

In one embodiment, the nanoparticle conjugate can be attached to at least one imaging agent (e.g., contrast agents). In some embodiments, the nanoparticle conjugate includes two or more different contrast agents so that two or more different imaging techniques can be used. Suitable contrast agents include, but are not limited to magnetic resonance imaging materials, electron spin resonance (ESR) materials, near infrared materials, PET materials, and the like. In some embodiments, the nanoparticle conjugate can itself be a moiety that provides a detectable signal (e.g., a quantum dot) in which case the nanoparticle/agent combination can provide at least two different detection modalities.

In certain embodiments, the nanoparticle conjugates of this invention can simply be used as detection agents (e.g., as MRI contrast agents). When coupled to a targeting entity they can, for example, be used to detect the presence, and/or location, and/or size of the target (e.g., a tumor cell or tumor mass or tissue) in vivo. In certain embodiments, the nanoparticle conjugates are used simply as therapeutic agents that, when coupled to a targeting entity, can be used to deliver a therapeutic moiety to a target cell or tissue. In certain embodiments, the nanoparticle conjugates are used both to image a target cell or tissue and to deliver one or more therapeutic moieties thereto.

In certain embodiments, methods are provided for imaging (e.g., detecting or quantifying the presence or absence, and/or the location and/or the size of a target) a tumor cell and/or tumor tissue. Similarly, in certain embodiments, methods are provided for delivering a therapeutic agent in proximity to, and/or on the surface of, and/or internalized into a tumor cell and/or tissue. In certain embodiments the methods involve using the nanoparticle conjugate to both image a target cell or tissue and to deliver a therapeutic moiety thereto.

i. Representative Imaging Agents

Imaging techniques such as MRI, PET, CT and X-ray involve the use of imaging agents which are designed to provide more information about internal organs, cellular processes and tumors as well as normal tissue. They can also be used to diagnose disease as well as monitor treatment effects. In one embodiment, the nanoparticle conjugates can be attached to one or more imaging agents to provide a multimodal probe. In various embodiments the imaging agent comprises an imaging agent for Magnetic resonance imaging (MRI), a PET imaging agent, X-ray, CT and ultrasonic imaging.

MRI imaging agents can include, but are not limited to positive contrast agents and/or negative contrast agents. Positive contrast agents cause a reduction in the $T_1$ relaxation time (increased signal intensity on $T_1$ weighted images). Positive contrast agents appear bright on MRI and are typically small molecular weight compounds containing as their active element gadolinium, manganese, or iron. All of these elements have unpaired electron spins in their outer shells and long relaxivities. A special group of negative contrast agents (appearing dark on MRI) include perfluorocarbons (perfluorochemicals), because their presence excludes the hydrogen atoms responsible for the signal in MR imaging.

MRI is widely used clinically because it provides high spatial resolution images, particularly through the application of contrast agents which are currently employed in approximately 35% of all clinical MRI examinations. These are typically derived from iron particles or paramagnetic, predominantly Gd, complexes. One of the clinically approved, and commonly used contrast agents are Gd-DOTA (DOTA=1,4,7,10-tetrakis(carboxymethyl)-1,4,7,10-tetraazacyclodode-cane), which shows low toxicity and patient discomfort. Clinical safety results from its low osmolality, low viscosity, low chemotoxicity, high solubility, and high in vivo stability for the macrocylic complex.

The vast majority of MRI applications depend on the bulk biodistribution of the contrast agent rather than molecular targeting methods. As a small molecule, Gd agents get into the microvasculature around tumors, which is at a much higher density than normal tissue. This increased concentration of Gd in highly vascularized tissue around tumors is the basis for the MRI contrast mechanism. Thus, specifically targeted contrast agents, as described herein, are extremely useful for improving the ability of MRI to localize cancer.

In certain embodiments, the MRI imaging or detection agent attached to the present multimodal probes are iron or paramagnetic radiotracers and/or complexes, including but not limited to gadolinium, xenon, iron oxide, copper, $Gd^{3+}$-DOTA, and $^{64}Cu^{2+}$-DOTA.

Positron Emission Tomagraphy (PET) Imaging Agents typically used in a PET scan are radioactive contrast agent and are especially useful in showing how tissue or an organ is functioning, as opposed to just showing structure. In a PET scan, radioactive atoms are introduced into the body. The positrons emit when radionuclei decay, collide and annihilate with electrons in surrounding tissue, producing a pair of gamma ray photons moving in opposite directions, allowing gamma ray origin in the body be plotted and the density of the isotope in the body mapped by pair-detection events.

In one embodiment, the nanoparticle conjugates are attached to one or more PET imaging agents. Representative PET imaging radionuclides include, without limitation, PET radiopharmaceuticals such as [$^{11}$C]choline, [$^{18}$F]fluorodeoxyglucose (FDG), [$^{11}$C]methionine [$^{11}$C]choline, [$^{11}$C]acetate, and [$^{18}$F]fluorocholine as well as other radionuclides including but not limited to $^{11}$C, $^{15}$O, $^{13}$N, $^{18}$F, $^{35}$Cl, $^{75}$Br, $^{82}$Rb, $^{82}$Rb, $^{124}$I, $^{64}$Cu, $^{225}$Ac, $^{177}$Lu, $^{111}$In, $^{66}$Ga, $^{67}$Ga, $^{68}$Ga, Technetium-99m, Thallium, and the like.

X-ray and CT imaging agents work by increasing the density of tissues and thus blocking x-ray transmission. Typically, barium compounds, iodine compounds, metals, and other substances as contrast agents are used. For instance, nanoparticles can be labeled with Bismuth sulfide or iohexol as the contrast agent. Alternatively, metallic nanoparticles such as gold nanoparticles act as an intrinsic contrasting agent.

For ultrasound imaging, any suitable contrast agent can be used. A representative example includes Optison.

Photoacoustic imaging exploits the photoacoustic effect where non-ionizing laser pulses are delivered to biological tissue where it is absorbed and converted into heat which in turn generates ultrasonic emission. Non-limiting representative photoacoustic imaging agents include gold nanoparticles and single-wall carbon nanotubes bound to dye contrast agents such as indocyanine green.

IV. Diagnostic System Overview

A diagnostic system can non-invasively detect and measure a plurality of physiological parameters of a person, which can include any parameters that may relate to the person's health. For example, the system could include sensors for measuring blood pressure, pulse rate, skin temperature, etc. At least some of the physiological parameters may be obtained by the system non-invasively detecting and/or measuring one or more analytes in blood circulating in subsurface vasculature. The one or more analytes could be any analytes that, when present in or absent from the blood, or present at a particular concentration or range of concentrations, may be indicative of a medical condition or health of the person. For example, the one or more analytes could include enzymes, hormones, proteins, drug metabolites, tumor cells, tumor markers or other molecules.

In an example embodiment, the system obtains at least some of the health-related information by detecting the binding or interaction of a clinically-relevant analyte to or with materials such as nanoparticles, introduced into a lumen of the subsurface vasculature that have been functionalized with an targeting entity that has a specific affinity to bind to or interact with the specific analyte such as a tumor marker. The term "binding" is understood in its broadest sense to also include a detectable interaction between the clinically relevant analyte and the nanoparticle conjugates. The nanoparticle conjugates can be introduced into the person's blood stream by injection, ingestion, inhalation, transdermally, or in some other manner.

The nanoparticles can be functionalized by covalently or otherwise attaching or associating a targeting entity that specifically binds, undergoes cell uptake or otherwise interacts with a particular clinically-relevant tumor cell as the target analyte with a defined affinity to the target analyte. Other compounds or molecules, such as fluorophores or autofluorescent or luminescent markers or non-optical contrast agents (e.g. acoustic impedance contrast, RF contrast and the like), which may assist in interrogating the nanoparticles in vivo, may also be attached to the nanoparticles.

The nanoparticles can have a diameter that is generally equal to or less than about 200 micrometers. In some embodiments, the nanoparticles have a diameter on the order of about 10 nanometers to 1 micrometer. In further embodiments, small nanoparticles on the order of 10-100 nanometers in diameter may be assembled to form a larger "clusters" or "assemblies on the order of 1-10 micrometers. Those of skill in the art will understand a "particle" in its broadest sense and that it may take the form of any fabricated material, a molecule, tryptophan, a virus, a phage, etc. Further, a particle may be of any shape, for example, spheres, rods, non-symmetrical shapes, etc.

In some examples, the nanoparticles may also be magnetic and can be formed from a paramagnetic, super-paramagnetic or ferromagnetic material or any other material that responds to a magnetic field. Alternatively, the nanoparticles may also be made of non-magnetic materials such as polystyrene. Where magnetic nanoparticles are used, the system may include a magnet that can direct into the portion of subsurface vasculature a magnetic field that is sufficient to manipulate aptamer-magnetic particle conjugates in a lumen of that portion of subsurface vasculature, for example, to collect or slow down in a certain area. However, measurements may be taken without localized "collection" of the nanoparticle conjugates. The system may be configured to activate the magnetic periodically, such as at certain times of the day (e.g., every hour).

The system may further include one or more data collection systems for interrogating, in a non-invasive manner, the nanoparticle conjugates present in a lumen of the subsurface vasculature in a particular local area. In one example, the system includes a detector configured to detect a response signal transmitted from a portion of subsurface vasculature. The response signal can include both an analyte response signal, which can be related to the interaction of the one or more target analytes with the nanoparticle conjugates, and a background noise signal. For example, the nanoparticle conjugates may include a chemiluminescent marker configured to produce a response signal in the form of luminescence radiation produced in response to a chemical reaction initiated, at least in part, to the binding of the target analyte to the particle.

In some examples, the system may also include an interrogating signal source for transmitting an interrogating signal that can penetrate into a portion of subsurface vasculature, or another body system, and a detector for detecting a response signal that is transmitted from the portion of subsurface vasculature, or other body system, in response to the interrogating signal. The interrogating signal can be any kind of signal that is benign to the patient, such as electromagnetic, magnetic, optic, acoustic, thermal, mechanical, electric and results in a response signal that can be used to measure a physiological parameter or, more particularly, that can detect the binding or interaction of the clinically-relevant analyte to the nanoparticle conjugates. In one example, the interrogating signal is a radio frequency (RF) signal and the response signal is a magnetic resonance signal, such as nuclear magnetic resonance (NMR). In another example, where the nanoparticle conjugates include a fluorophore, the interrogating signal is an optical signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector. In another example, where the nanoparticle conjugates include an electrically conductive material or a magnetically lossy material, the interrogation signal may be a time-varying magnetic field or a radio frequency (RF) electromagnetic signal, with sufficient signal power to rapidly heat the nanoparticles. The response signal may be an acoustic emission from the nanoparticles, caused by rapid thermal expansion of the nanoparticles, or caused by cavitation of the liquid medium in contact with the nanoparticles. As described above, in some cases, an interrogating signal may not be necessary to produce an analyte response signal.

Additionally, the system may further include a modulation source configured to modulate the analyte response signal. The modulation source can be configured to modulate the analyte response signal differently than the background noise signal. To this end, the modulation may help to discern between the target analyte and, essentially, everything else in the body by, for example, increasing the signal-to-noise ratio. Generally, the modulation may include any spatial, temporal, spectral, thermal, magnetic, mechanical, electrical, acoustic, chemical, or electrochemical, etc. modulation technique or any combination thereof.

In some scenarios, it may also be useful to detect and distinguish both the analyte response signal—related to nanoparticle conjugates bound to or interacting with target analyte(s)—and an "unbound" particle signal—related to nanoparticle conjugates not bound to or interacting with target analyte(s). For example, in some measurement or characterization schemes, it may be useful to determine the percentage of nanoparticle conjugates introduced into the body that have bound to the target analyte. In such cases, the modulation source may be configured to modulate the analyte response signal differently than the unbound particle signal.

Data collected by the detector may be sent to a processor for analysis. The processor may be configured to non-invasively detect the one or more target analytes by differentiating the analyte response signal from the background noise signal based, at least in part, on the modulation. In some cases, the processor may further be configured to differentiate the analyte response signal from the unbound particle signal. Further, the processor may be configured to determine the concentration of a particular target analyte in the blood from, at least in part, the analyte response signal. The detection and concentration data processed by the processor may be communicated to the patient, transmitted to medical or clinical personnel, locally stored or transmitted to a remote server, the cloud, and/or any other system where the data may be stored or accessed at a later time.

The processor may be located on an external reader, which may be provided as an external body-mounted device, such as a necklace, wristwatch, eyeglasses, a mobile phone, a handheld or personal computing device or some combination thereof. Data collected by the detector may be transmitted to the external reader via a communication interface. Control electronics can wirelessly communicate the data to the external reader by modifying the impedance of an antenna in communication with the detector so as to characteristically modify the backscatter from the antenna. In some examples, the external reader can operate to intermittently interrogate the detector to provide a reading by radiating sufficient radiation to power the detector to obtain a measurement and communicate the result. In this way, the external reader can acquire a series of analyte identification and concentration measurements over time without continuously powering the detector and/or processor. The processor may also be provided at another location distal to the detector, and the detector data is communicated to the processor via a wired connection, a memory card, a USB device or other known method. Alternatively, the processor may be located proximal to the detector and may be configured to locally analyze the data that it collects and then transmit the results of the analysis to an external reader or server.

The external reader may include a user interface, or may further transmit the collected data to a device with a user interface that can indicate the results of the data analysis. In this way, the person wearing, holding or viewing the device can be made aware of the analysis and/or potential medical conditions. The external reader may also be configured to produce an auditory or tactile (vibration) response to alert the patient of a medical condition. Further, the external reader may also be configured to receive information from the patient regarding his/her health state, wellness state, activity state, nutrition intake and the like, as additional input information to the processor. For example, the user may input a health or wellness state, such as, experiencing migraine symptoms, jittery, racing heart, upset stomach, feeling tired, activity state including types and duration of physical activity nutrition intake including meal timing and composition, and other parameters including body weight, medication intake, quality of sleep, stress level, personal care products used, environmental conditions, social activity, etc. Further, the reader may also receive signals from one or more other detectors, such as a pedometer, heart rate sensor, blood pressure sensor, blood oxygen saturation level, body temperature, GPS or other location or positioning sensors, microphone, light sensor, etc.

The system may be configured to obtain data during pre-set measurement periods or in response to a prompt. For example, the system may be configured to operate the detector and collect data once an hour. In other examples, the system may be configured to operate the detector in response to a prompt, such as a manual input by the patient or a physician. The system may also be configured to obtain data in response to an internal or external event or combination of events, such as during or after physical activity, at rest, at high pulse rates, high or low blood pressures, cold or hot weather conditions, etc. In other examples, the system could operate the detector more frequently or less frequently, or the system could measure some analytes more frequently than others.

Data collected by the system may be used to notify the patient of, as described above, analyte levels or of an existing or imminent medical emergency. In some examples, the data may be used to develop an individual baseline profile for the patient. The baseline profile may include patterns for how one or more of the patient's analyte levels typically change over time, such as during the course of a day, a week, or a month, or in response to consumption of a particular type of food/drug. The baseline profile, in essence, may establish "normal" levels of the measured analytes for the patient. Additional data, collected over additional measurement periods, may be compared to the baseline profile. If the additional data is consistent with the patterns embodied in the baseline profile, it may be determined that the patient's condition has not changed. On the other hand, if the additional data deviates from the patterns embodied in the baseline profile, it may be determined that the patient's condition has changed. The change in condition could, for example, indicate that the patient has developed a disease, disorder, or other adverse medical condition or may be at risk for a severe medical condition in the near future. Further, the change in condition could further indicate a change in the patient's eating habits, either positively or negatively, which could be of interest to medical personnel. Further, the patient's baseline and deviations from the baseline can be compared to baseline and deviation data collected from a population of wearers of the devices.

When a change in condition is detected, a clinical protocol may be consulted to generate one or more recommendations that are appropriate for the patient's change in condition. For example, it may be recommended that the patient inject himself/herself with insulin, change his/her diet, take a particular medication or supplement, schedule an appointment with a medical professional, get a specific medical test, go to the hospital to seek immediate medical attention, abstain from certain activities, etc. The clinical protocol may be developed based, at least in part, on correlations between analyte concentration and health state derived by the server, any known health information or medical history of the patient, and/or on recognized standards of care in the medical field. The one or more recommendations may then be transmitted to the external reader for communication to the user via the user interface.

Correlations may be derived between the analyte concentration(s) measured by the system and the health state reported by the patient. For example, analysis of the analyte data and the health state data may reveal that the patient has not responded to chemotherapy when an analyte reaches a certain concentration. This correlation data may be used to generate recommendations for the patient, or to develop a clinical protocol. Blood analysis may be complemented with other physiological measurements such as blood pressure, heart rate, body temperature etc., in order to add to or enhance these correlations.

Further, data collected from a plurality of patients, including both the analyte measurements and the indications of health state, may be used to develop one or more clinical protocols used by the server to generate recommendations and/or used by medical professionals to provide medical care and advice to their patients. This data may further be used to recognize correlations between blood analytes and health conditions among the population. Health professionals may further use this data to diagnose and prevent illness and disease, prevent serious clinical events in the population, and to update clinical protocols, courses of treatment, and the standard of care.

The above described system may be implemented as a device. In one embodiment, the device is a wearable device. The term "wearable device," as used in this disclosure, refers to any device that is capable of being worn at, on or in proximity to a body surface, such as a wrist, ankle, waist, chest, ear, eye or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount, such as a belt, wristband, ankle band, headband, etc. can be provided to mount the device at, on or in proximity to the body surface. The mount may prevent the wearable device from moving relative to the body to reduce measurement error and noise. Further, the mount may be an adhesive substrate for adhering the wearable device to the body of a wearer. The detector, modulation source, interrogation signal source (if applicable) and, in some examples, the processor, may be provided on the wearable device. In other embodiments, the above described system may be implemented as a stationary measurement device to which a user must be brought into contact or proximity with or as a device that may be temporarily placed or held against a body surface during one or more measurement periods.

It should be understood that the above embodiments, and other embodiments described herein, are provided for explanatory purposes, and are not intended to be limiting.

V. Example Wearable Devices

In some examples, the wearable devices described herein obtain at least some of the health-related information by detecting the binding of a clinically-relevant analyte such as a tmor marker to the nanoparticle conjugates. The nanoparticle conjugates can be introduced into the person's blood stream by injection, ingestion, inhalation, transdermally, or in some other suitable manner.

Figure 4:
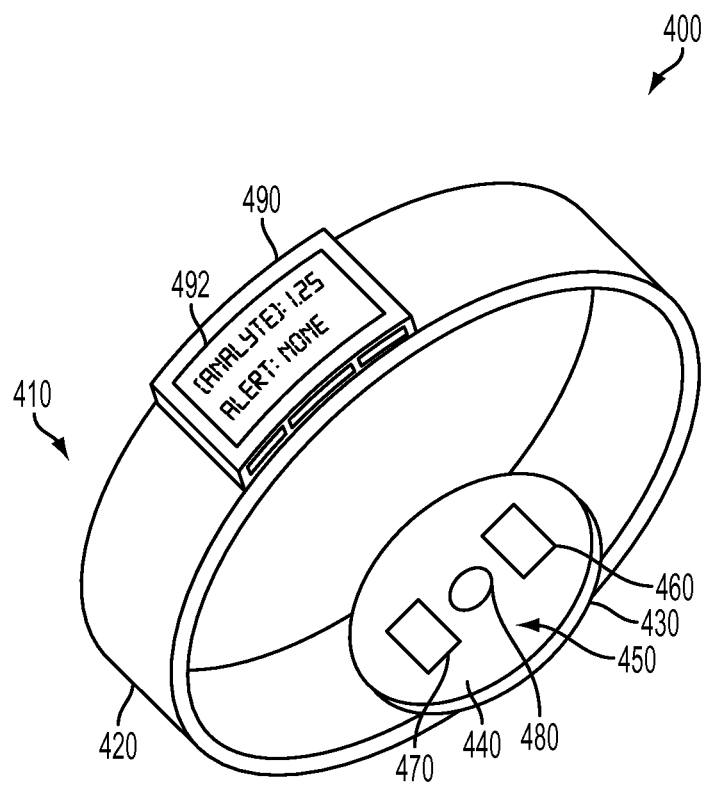
FIG. 4 is a perspective view of an example wearable device.

A wearable device 400 can automatically measure a plurality of physiological parameters of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount 410, such as a belt, wristband, ankle band, etc. can be provided to mount the device at, on or in proximity to the body surface. The mount 410 may prevent the wearable device from moving relative to the body to reduce measurement error and noise. In one example, shown in FIG. 4, the mount 410, may take the form of a strap or band 420 that can be worn around a part of the body. Further, the mount 410 may be an adhesive substrate for adhering the wearable device 400 to the body of a wearer.

A measurement platform 430 is disposed on the mount 410 such that it can be positioned on the body where subsurface vasculature is easily observable. An inner face 440 of the measurement platform is intended to be mounted facing to the body surface. The measurement platform 430 may house a data collection system 450, which may include at least one detector 460 for detecting at least one physiological parameter. The at least one physiological parameter could be any parameter that may relate to the health of the person wearing the wearable device. For example, the detector 460 could be configured to measure blood pressure, pulse rate, respiration rate, skin temperature, etc. At least one of the detectors 460 is configured to non-invasively measure one or more analytes in blood circulating in subsurface vasculature proximate to the wearable device. In a non-exhaustive list, detector 460 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance)

sensor. The components of the data collection system 450 may be miniaturized so that the wearable device may be worn on the body without significantly interfering with the wearer's usual activities.

In some examples, the data collection system 450 further includes a signal source 470 for transmitting an interrogating signal that can penetrate the wearer's skin into the portion of subsurface vasculature, for example, into a lumen of the subsurface vasculature. The interrogating signal can be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the nanoparticle conjugates. In one example, the interrogating signal is an electromagnetic pulse (e.g., a radio frequency (RF) pulse) and the response signal is a magnetic resonance signal, such as nuclear magnetic resonance (NMR). In another example, the interrogating signal is a time-varying magnetic field, and the response signal is an externally-detectable physical motion due to the time-varying magnetic field. The time-varying magnetic field modulates the nanoparticles by physical motion in a manner different from the background, making them easier to detect. In a further example, the interrogating signal is an electromagnetic radiation signal. In particular, the interrogating signal may be electromagnetic radiation having a wavelength between about 400 nanometers and about 1600 nanometers. The interrogating signal may, more particularly, comprise electromagnetic radiation having a wavelength between about 500 nanometers and about 1000 nanometers. In some examples, the nanoparticle conjugates include a fluorophore. The interrogating signal may therefore be an electromagnetic radiation signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector.

In some cases, an interrogating signal is not necessary to measure one or more of the physiological parameters and, therefore, the wearable device 400 may not include a signal source 470. For example, the nanoparticle conjugates include an autofluorescent or luminescent marker, such as a fluorophore, that will automatically emit a response signal indicative of the binding of the clinically-relevant analyte to the nanoparticle conjugates, without the need for an interrogating signal or other external stimulus. In some examples, the nanoparticle conjugates may include a chemiluminescent marker configured to produce a response signal in the form of luminescence radiation produced in response to a chemical reaction initiated, at least in part, to the binding of the target analyte to the particle.

A collection magnet 480 may also be included in the data collection system 450. In such embodiments, the nanoparticle conjugates may also be made of or be functionalized with magnetic materials, such as ferromagnetic, paramagnetic, super-paramagnetic, or any other material that responds to a magnetic field. The collection magnet 480 is configured to direct a magnetic field into the portion of subsurface vasculature that is sufficient to cause the magnetic nanoparticle conjugates to collect in a lumen of that portion of subsurface vasculature. The magnet may be an electromagnet that may be turned on during measurement periods and turned off when a measurement period is complete so as to allow the magnetic nanoparticles to disperse through the vasculature.

The wearable device 400 may also include a user interface 490 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 490 may include a display 492 where a visual indication of the alert or recommendation may be displayed. The display 492 may further be configured to provide an indication of the measured physiological parameters, for instance, the concentrations of certain blood analytes being measured.

The wearable device may, in some cases, also include a modulation source. The signal-to-noise ratio (SNR) in an analyte detection system, such as any of those described above, may be increased by modulating the analyte response signal transmitted from the subsurface vasculature (or other body system) with respect to the background signal and, in some cases, an unbound particle response signal. Such modulation can increase the system's sensitivity and ability to discern between target analytes present in the blood or other bodily fluids, versus other analytes, nanoparticles, cells, molecules, blood components, bone and tissues, etc. This can be particularly valuable with some methods of analyte characterization, such as optical methods, or where the target analytes are rare in the blood or are of a relatively small size and with fluorescence detection techniques, which can often suffer from low resolution because other tissues, cells, and molecules in the body may have some inherent fluorescent properties, creating a high level of background noise.

The modulation source may apply a modulation, configured to modulate the response signal, to the portion of the body. Specifically, the modulation source may be configured to modulate the analyte response signal differently from a background signal. The background signal may include any signal transmitted from something other than what the system is monitoring, i.e., the target analyte(s). In some examples, the background signal may be generated by other molecules, cells, or nanoparticles in the blood or other bodily fluids; tissue, such as skin, veins, muscle, etc.; bone; or other objects present in the wearer's body. A background signal may be generated by excitation of these objects from the interrogating signal, such as by generating an autofluorescence signal, or due to some inherent property of these objects, such as, chemiluminescence, etc.

In some examples, the modulation source may be configured to modulate the analyte response signal (transmitted from bound nanoparticles) differently than the unbound particle signal (transmitted from nanoparticles that are not bound or otherwise interacting with the target analyte(s)), such that the analyte response signal may be differentiated from the unbound particle signal. Such differentiation may be used to determine the number or percentage of nanoparticles bound to or interacting with the target analyte(s), which may be used to determine a concentration of the target analyte(s) in the blood or other bodily fluid, to determine if and to what extent the nanoparticles are being cleared from the body, etc.

The modulation source may include any means for modulating the response signal. In some cases, the analyte response signal may be modulated differently than the background signal, and in other cases the analyte response signal may be modulated differently than the unbound particle signal, or both. For example, the modulation source may be configured to alter the spatial, optical magnetic, electric, acoustic, and/or physical properties of the bound nanoparticles. The modulation source may be a physical construct or it may be a signal or energy applied to the body, or a combination thereof. Accordingly, the modulation may include spatial, temporal, spectral, thermal, magnetic, optical, mechanical, electrical, acoustic, chemical, or electrochemical type of modulation or any combination thereof.

Figure 5A:
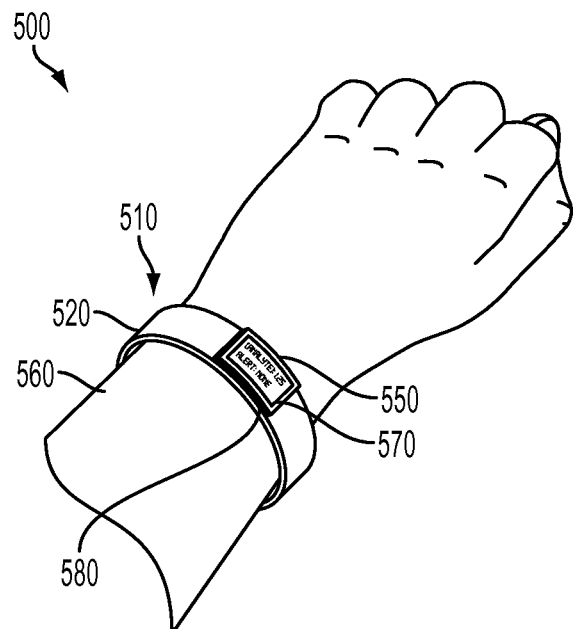
FIG. 5A is a perspective top view of an example wrist-mounted device, when mounted on a wearer's wrist.
Figure 5B:
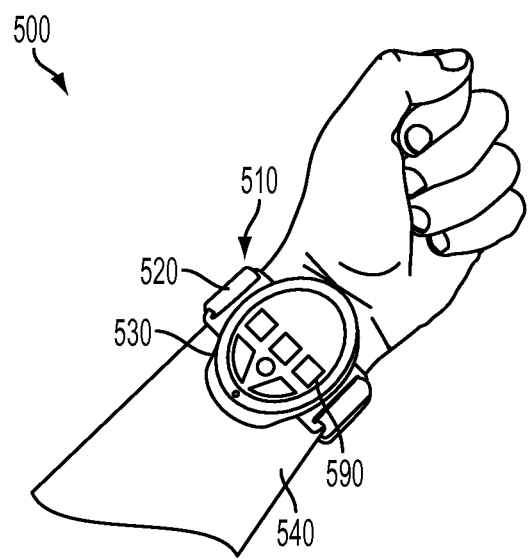
FIG. 5B is a perspective bottom view of an example wrist-mounted device shown in FIG. 2A, when mounted on a wearer's wrist.

In one example, the wearable device is provided as a wrist-mounted device, as shown in FIGS. 5A, 5B, 6A-6C, 7A, 8B, and 9. The wrist-mounted device may be mounted to the wrist of a living subject with a wristband or cuff, similar to a watch or bracelet. As shown in FIGS. 5A and 5B, the wrist mounted device 500 may include a mount 510 in the form of a wristband 520, a measurement platform 530 positioned on the anterior side 540 of the wearer's wrist, and a user interface 550 positioned on the posterior side 560 of the wearer's wrist. The wearer of the device may receive, via the user interface 550, one or more recommendations or alerts generated either from a remote server or other remote computing device, or alerts from the measurement platform. Such a configuration may be perceived as natural for the wearer of the device in that it is common for the posterior side 560 of the wrist to be observed, such as the act of checking a wrist-watch. Accordingly, the wearer may easily view a display 570 on the user interface. Further, the measurement platform 530 may be located on the anterior side 540 of the wearer's wrist where the subsurface vasculature may be readily observable. However, other configurations are contemplated.

The display 570 may be configured to display a visual indication of the alert or recommendation and/or an indication of the measured physiological parameters, for instance, the concentrations of certain blood analytes being measured. Further, the user interface 550 may include one or more buttons 580 for accepting inputs from the wearer. For example, the buttons 580 may be configured to change the text or other information visible on the display 570. As shown in FIG. 5B, measurement platform 530 may also include one or more buttons 590 for accepting inputs from the wearer. The buttons 590 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

Figure 6A:
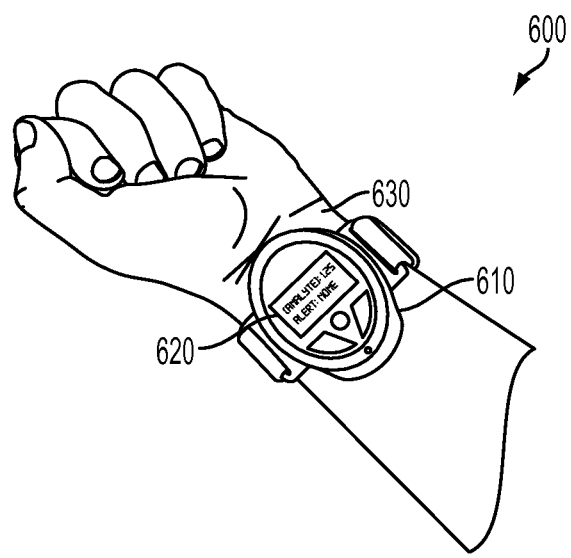
FIG. 6A is a perspective bottom view of an example wrist-mounted device, when mounted on a wearer's wrist.
Figure 6B:
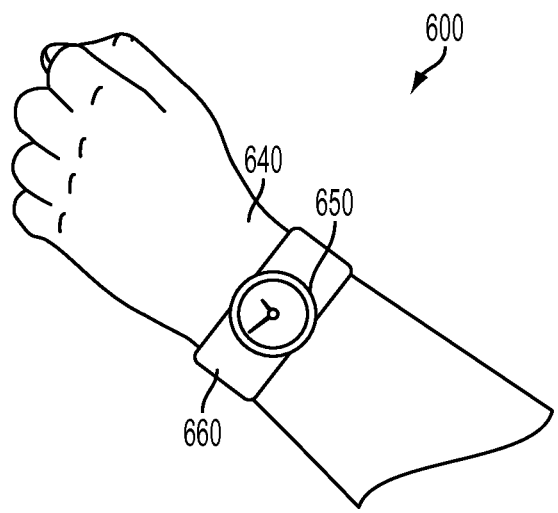
FIG. 6B is a perspective top view of an example wrist-mounted device shown in FIG. 6A, when mounted on a wearer's wrist.
Figure 6C:
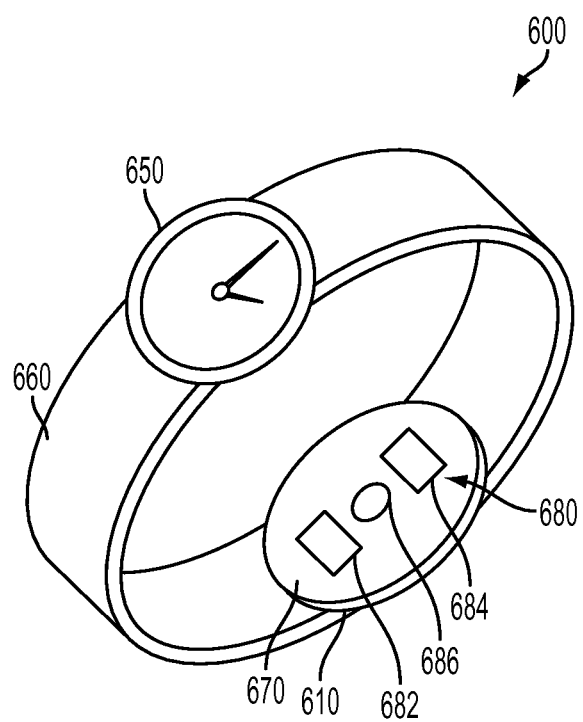
FIG. 6C is a perspective view of an example wrist-mounted device shown in FIGS. 6A and 6B.

In another example wrist-mounted device 600, shown in FIGS. 6A-6C, the measurement platform 610 and user interface 620 are both provided on the same side of the wearer's wrist, in particular, the anterior side 630 of the wrist. On the posterior side 640, a watch face 650 may be disposed on the strap 660. While an analog watch is depicted in FIG. 6B, one of ordinary skill in the art will recognize that any type of clock may be provided, such as a digital clock.

As can be seen in FIG. 6C, the inner face 670 of the measurement platform 610 is intended to be worn proximate to the wearer's body. A data collection system 680 housed on the measurement platform 610 may include a detector 682, a signal source 684 and a collection magnet 686. As described above, the signal source 684 and the collection magnet 686 may not be provided in all embodiments of the wearable device.

Figure 7A:
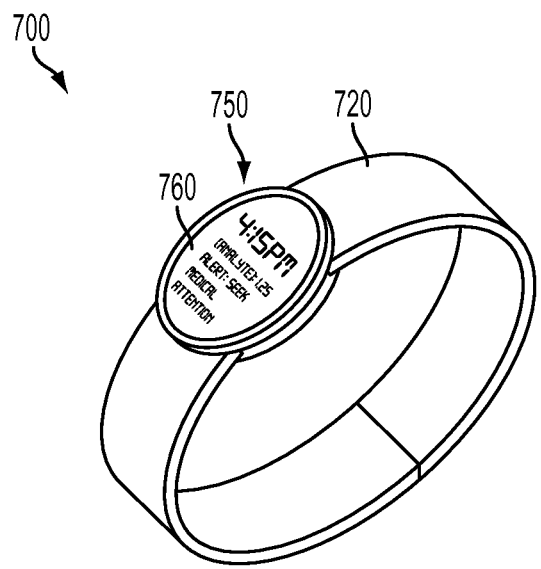
FIG. 7A is a perspective view of an example wrist-mounted device.
Figure 7B:
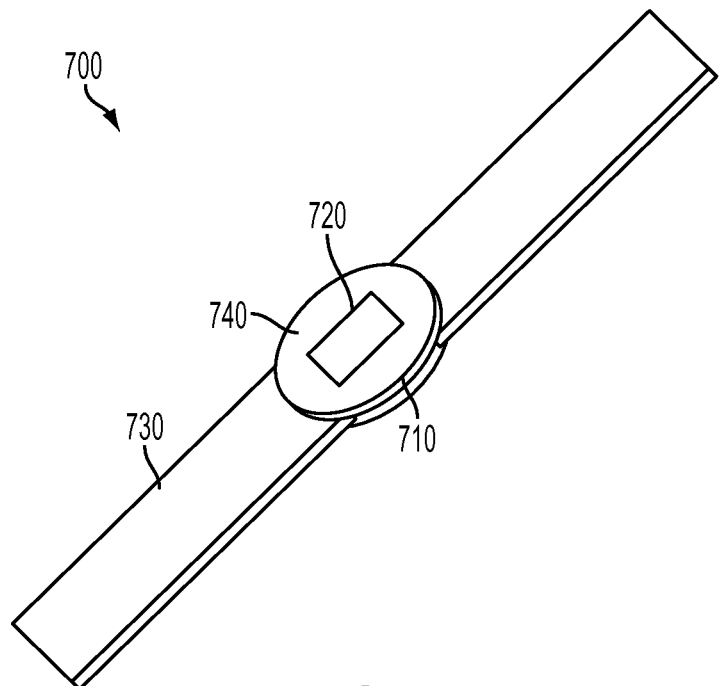
FIG. 7B is a perspective bottom view of an example wrist-mounted device shown in FIG. 7A.

In a further example shown in FIGS. 7A and 7B, a wrist mounted device 700 includes a measurement platform 710, which includes a data collection system 720, disposed on a strap 730. Inner face 740 of measurement platform may be positioned proximate to a body surface so that data collection system 720 may interrogate the subsurface vasculature of the wearer's wrist. A user interface 750 with a display 760 may be positioned facing outward from the measurement platform 710. As described above in connection with other embodiments, user interface 750 may be configured to display data collected from the data collection system 720, including the concentration of one or more measured analytes, and one or more alerts generated by a remote server or other remote computing device, or a processor located on the measurement platform. The user interface 720 may also be configured to display the time of day, date, or other information that may be relevant to the wearer.

Figure 8:
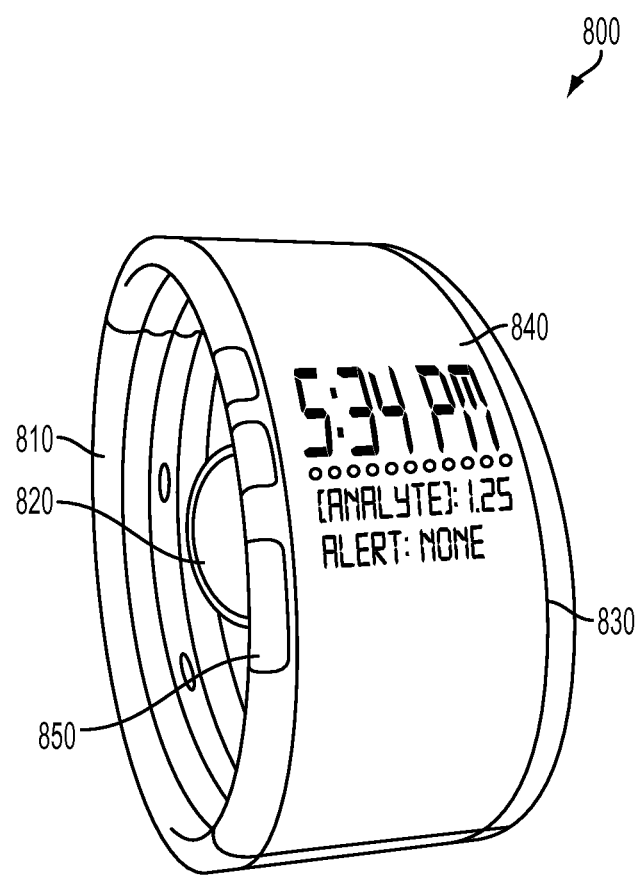
FIG. 8 is a perspective view of an example wrist-mounted device.
Figure 9:
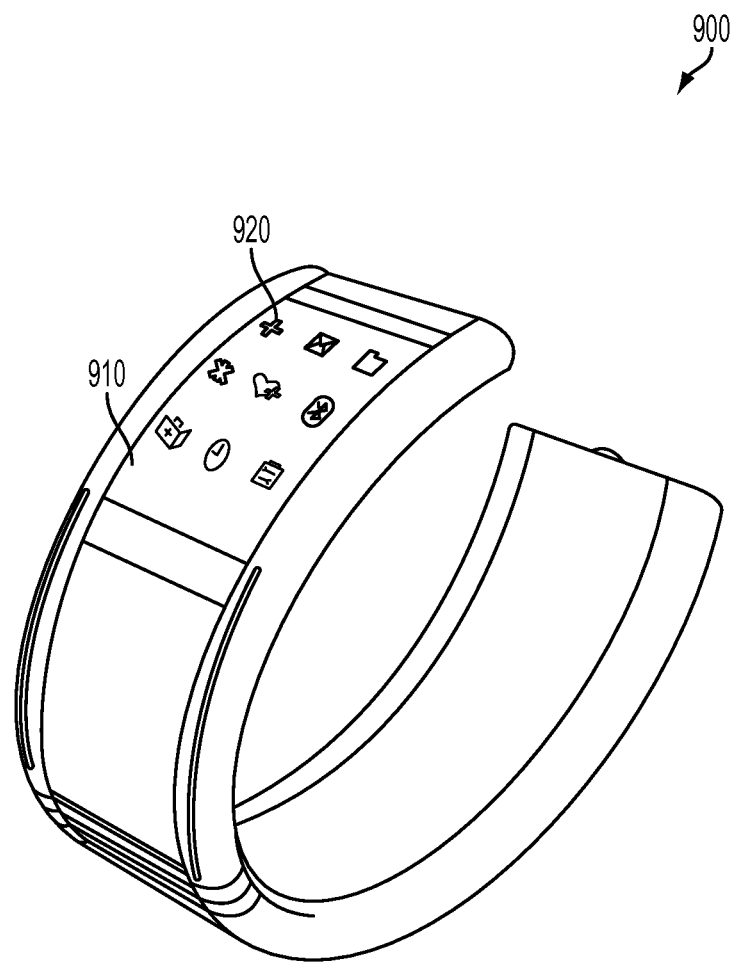
FIG. 9 is a perspective view of an example wrist-mounted device.

As shown in FIG. 8, in a further embodiment, wrist-mounted device 800 may be provided on a cuff 810. Similar to the previously discussed embodiments, device 800 includes a measurement platform 820 and a user interface 830, which may include a display 840 and one or more buttons 850. The display 840 may further be a touch-screen display configured to accept one or more input by the wearer. For example, as shown in FIG. 9, display 910 may be a touch-screen configured to display one or more virtual buttons 920 for accepting one or more inputs for controlling certain functions or aspects of the device 900, or inputs of information by the user, such as current health state.

Figure 10:
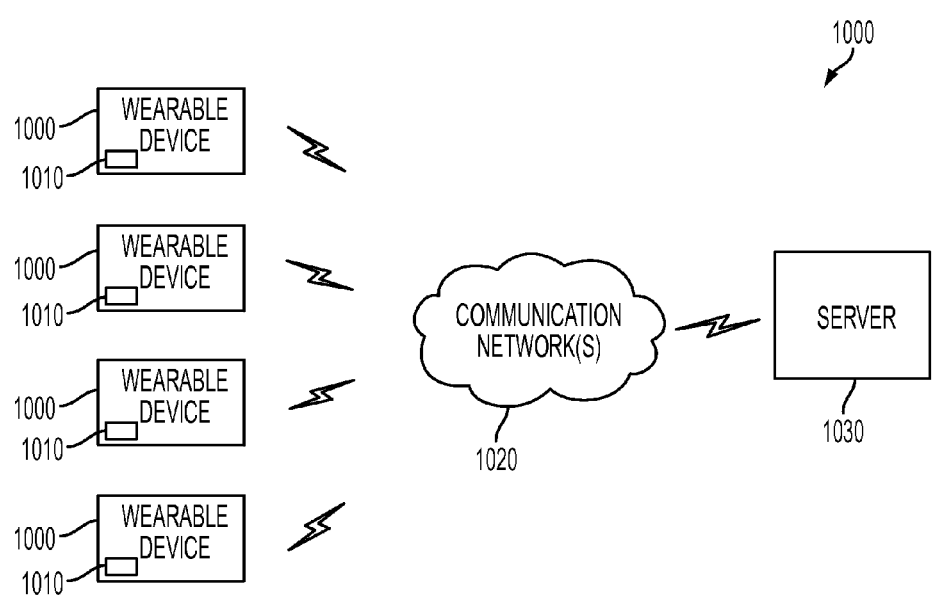
FIG. 10 is a block diagram of an example system that includes a plurality of wearable devices in communication with a server.

FIG. 10 is a simplified schematic of a system including one or more wearable devices 1000. The one or more wearable devices 1000 may be configured to transmit data via a communication interface 1010 over one or more communication networks 1020 to a remote server 1030. In one embodiment, the communication interface 1010 includes a wireless transceiver for sending and receiving communications to and from the server 1030. In further embodiments, the communication interface 1010 may include any means for the transfer of data, including both wired and wireless communications. For example, the communication interface may include a universal serial bus (USB) interface or a secure digital (SD) card interface. Communication networks 1020 may be any one of may be one of: a plain old telephone service (POTS) network, a cellular network, a fiber network and a data network. The server 1030 may include any type of remote computing device or remote cloud computing network. Further, communication network 1020 may include one or more intermediaries, including, for example wherein the wearable device 1000 transmits data to a mobile phone or other personal computing device, which in turn transmits the data to the server 1030.

In addition to receiving communications from the wearable device 1000, such as collected physiological parameter data and data regarding health state as input by the user, the server may also be configured to gather and/or receive either from the wearable device 1000 or from some other source, information regarding a wearer's overall medical history, environmental factors and geographical data. For example, a user account may be established on the server for every wearer that contains the wearer's medical history. Moreover, in some examples, the server 1030 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure tumor marker concentrations. If a wearer is prescribed a drug intended to treat cancer, but the server receives data from the wearable device indicating that the wearer's tumor marker concentration has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

VI. Example Electronics Platform for a Wearable Device

Figure 11:
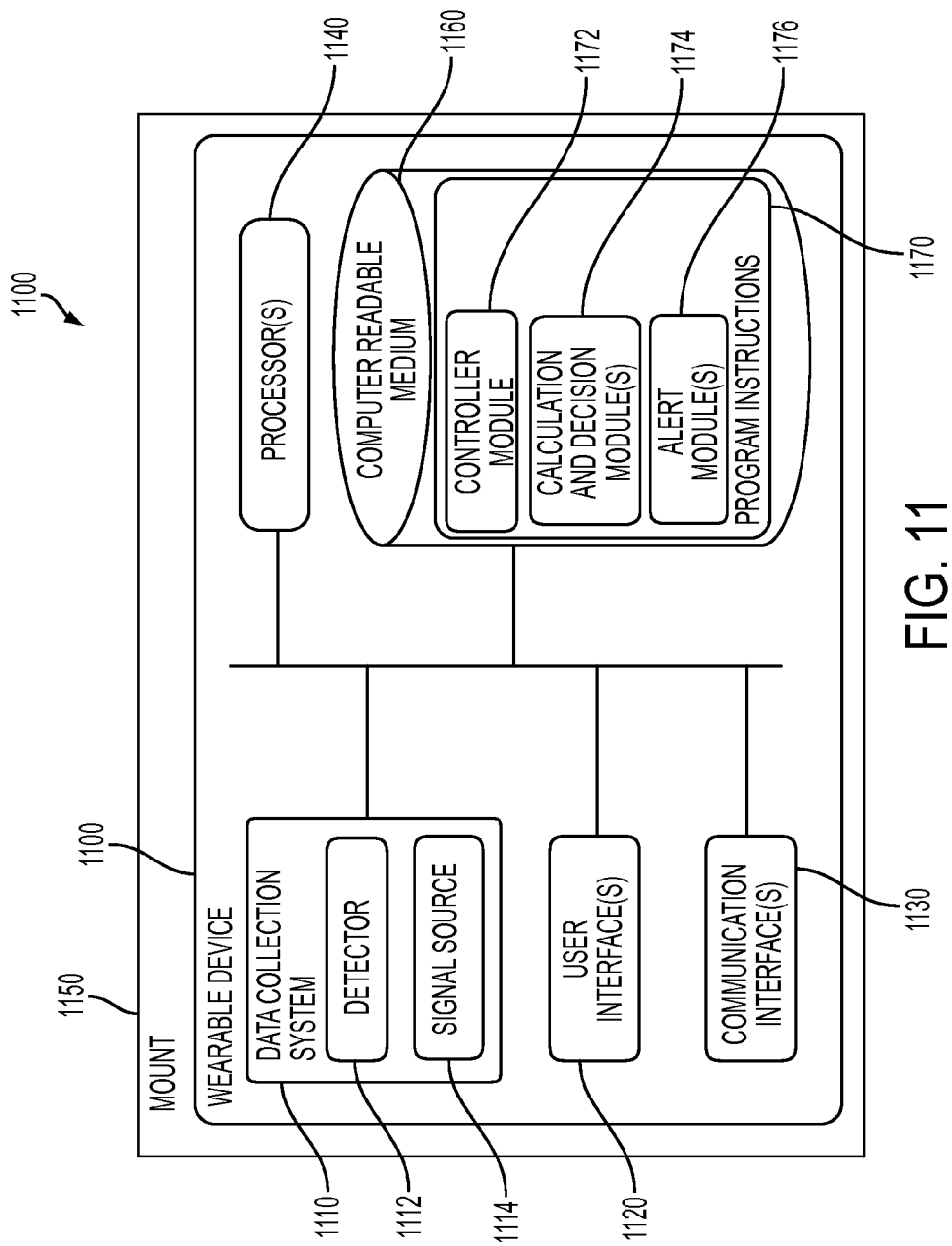
FIG. 11 is a functional block diagram of an example wearable device.

FIG. 11 is a simplified block diagram illustrating the components of a wearable device 1100, according to an example embodiment. Wearable device 800 may take the form of or be similar to one of the wrist-mounted devices 500, 600, 700, 800, 900, shown in FIGS. 5A-B, 6A-6C, 7A-7C, 8 and 9. However, wearable device 1100 may also take other forms, such as an ankle, waist, or chest-mounted device.

In particular, FIG. 11 shows an example of a wearable device 1100 having a data collection system 1110, a user interface 1120, communication platform 1130 for transmitting data to a server, and processor(s) 1140. The components of the wearable device 1100 may be disposed on a mount 1150 for mounting the device to an external body surface where a portion of subsurface vasculature is readily observable.

Processor 1140 may be a general-purpose processor or a special purpose processor (e.g., digital signal processors, application specific integrated circuits, etc.). The one or more processors 1140 can be configured to execute computer-readable program instructions 1170 that are stored in the computer readable medium 1160 and are executable to provide the functionality of a wearable device 1100 described herein.

The computer readable medium 1160 may include or take the form of one or more non-transitory, computer-readable storage media that can be read or accessed by at least one processor 1140. The one or more computer-readable storage media can include volatile and/or non-volatile storage components, such as optical, magnetic, organic or other memory or disc storage, which can be integrated in whole or in part with at least one of the one or more processors 1140. In some embodiments, the computer readable medium 1160 can be implemented using a single physical device (e.g., one optical, magnetic, organic or other memory or disc storage unit), while in other embodiments, the computer readable medium 1160 can be implemented using two or more physical devices.

Data collection system 1110 includes a detector 1112 and, in some embodiments, a signal source 1114. As described above, detector 1112 may include any detector capable of detecting at least one physiological parameter, which could include any parameters that may relate to the health of the person wearing the wearable device. For example, the detector 1112 could be configured to measure blood pressure, pulse rate, skin temperature, etc. At least one of the detectors 1112 is configured to non-invasively measure one or more analytes in blood circulating in subsurface vasculature proximate to the wearable device. In some examples, detector 1112 may include one or more of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

In some examples, the data collection system 1110 further includes a signal source 1114 for transmitting an interrogating signal that can penetrate the wearer's skin into the portion of subsurface vasculature. In general, signal source 1114 will generate an interrogation signal that will produce a responsive signal that can be detected by one or more of the detectors 1112. The interrogating signal can be any kind of signal that is benign to the wearer, such as electromagnetic, magnetic, optic, acoustic, thermal, mechanical, and results in a response signal that can be used to measure a physiological parameter or, more particularly, that can detect the binding of the clinically-relevant analyte to the nanoparticle conjugates. In one example, the interrogating signal is an electromagnetic pulse (e.g., a radio frequency (RF) pulse) and the response signal is a magnetic resonance signal, such as nuclear magnetic resonance (NMR). In another example, the interrogating signal is a time-varying magnetic field, and the response signal is an externally-detectable physical motion due to the time-varying magnetic field. The time-varying magnetic field modulates the nanoparticles by physical motion in a manner different from the background, making them easier to detect. In a further example, the interrogating signal is an electromagnetic radiation signal. In particular, the interrogating signal may be electromagnetic radiation having a wavelength between about 400 nanometers and about 1600 nanometers. The interrogating signal may, more particularly, comprise electromagnetic radiation having a wavelength between about 500 nanometers and about 1000 nanometers. In examples where the nanoparticle conjugates include a fluorophore, the interrogating signal may therefore be an electromagnetic radiation signal with a wavelength that can excite the fluorophore and penetrate the skin or other tissue and subsurface vasculature (e.g., a wavelength in the range of about 500 to about 1000 nanometers), and the response signal is fluorescence radiation from the fluorophore that can penetrate the subsurface vasculature and tissue to reach the detector.

The program instructions 1170 stored on the computer readable medium 1160 may include instructions to perform or facilitate some or all of the device functionality described herein. For instance, in the illustrated embodiment, program instructions 1170 include a controller module 1172, calculation and decision module 1174 and an alert module 1176.

The controller module 1172 can include instructions for operating the data collection system 1110, for example, the detector 1112 and signal source 1114. For example, the controller 1172 may activate signal source 1114 and/or detector 1112 during each of the pre-set measurement periods. In particular, the controller module 1172 can include instructions for controlling the signal source 1114 to transmit an interrogating signal at preset measurement times and controlling the detector 1112 to receive data representative of response signals transmitted from the portion of subsurface vasculature in response to the interrogating signals transmitted at the preset measurement times.

The controller module 1172 can also include instructions for operating a user interface 1120. For example, controller module 1172 may include instructions for displaying data collected by the data collection system 1110 and analyzed by the calculation and decision module 1174, or for displaying one or more alerts generated by the alert module 1175. Further, controller module 1172 may include instructions to execute certain functions based on inputs accepted by the user interface 1120, such as inputs accepted by one or more buttons disposed on the user interface.

Communication platform 1130 may also be operated by instructions within the controller module 1172, such as instructions for sending and/or receiving information via a wireless antenna, which may be disposed on or in the wearable device 1100. The communication interface 1130 can optionally include one or more oscillators, mixers, frequency injectors, etc. to modulate and/or demodulate information on a carrier frequency to be transmitted and/or received by the antenna. In some examples, the wearable device 1100 is configured to indicate an output from the processor by modulating an impedance of the antenna in a manner that is perceivable by a remote server or other remote computing device.

Calculation and decision module 1172 may include instructions for receiving data from the data collection system 1110 in the form of a responsive signal, analyzing the data to determine if the target analyte is present or absent, quantify the measured physiological parameter(s), such as concentration of a target analyte, and analyzing the data to determine if a medical condition is indicated. In particular, the calculation and decision module 1172 may include instructions for determining, for each preset measurement time, a concentration of a clinically-relevant analyte based on the response signal detected by the detector at that measurement time and determining, for each preset measurement time, whether a medical condition is indicated based on at least the corresponding concentration of the clinically-relevant analyte. The preset measurement times may be set to any period and, in one example, are about one hour apart.

The program instructions of the calculation and decision module 1172 may, in some examples, be stored in a computer-readable medium and executed by a processor located external to the wearable device. For example, the wearable device could be configured to collect certain data regarding physiological parameters from the wearer and then transmit the data to a remote server, which may include a mobile device, a personal computer, the cloud, or any other remote system, for further processing.

The computer readable medium 1160 may further contain other data or information, such as medical and health history of the wearer of the device, that may be useful in determining whether a medical condition is indicated. Further, the computer readable medium 1160 may contain data corresponding to certain analyte baselines, above or below which a medical condition is indicated. The baselines may be pre-stored on the computer readable medium 1160, may be transmitted from a remote source, such as a remote server, or may be generated by the calculation and decision module 1174 itself. The calculation and decision module 1174 may include instructions for generating individual baselines for the wearer of the device based on data collected over a certain number of measurement periods. For example, the calculation and decision module 1174 may generate a baseline concentration of a target blood analyte for each of a plurality of measurement periods by averaging the analyte concentration at each of the measurement periods measured over the course of a few days, and store those baseline concentrations in the computer readable medium 1160 for later comparison. Baselines may also be generated by a remote server and transmitted to the wearable device 1100 via communication interface 1130. The calculation and decision module 1174 may also, upon determining that a medical condition is indicated, generate one or more recommendations for the wearer of the device based, at least in part, on consultation of a clinical protocol. Such recommendations may alternatively be generated by the remote server and transmitted to the wearable device.

In some examples, the collected physiological parameter data, baseline profiles, health state information input by device wearers and generated recommendations and clinical protocols may additionally be input to a cloud network and be made available for download by a wearer's physician. Trend and other analyses may also be performed on the collected data, such as physiological parameter data and health state information, in the cloud computing network and be made available for download by physicians or clinicians.

Further, physiological parameter and health state data from individuals or populations of device wearers may be used by physicians or clinicians in monitoring efficacy of a drug or other treatment. For example, high-density, real-time data may be collected from a population of device wearers who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 1174 that a medical condition is indicated, the alert module 1176 may generate an alert via the user interface 1120. The alert may include a visual component, such as textual or graphical information displayed on a display, an auditory component (e.g., an alarm sound), and/or tactile component (e.g., a vibration). The textual information may include one or more recommendations, such as a recommendation that the wearer of the device contact a medical professional, seek immediate medical attention, or administer a medication.

Figure 12:
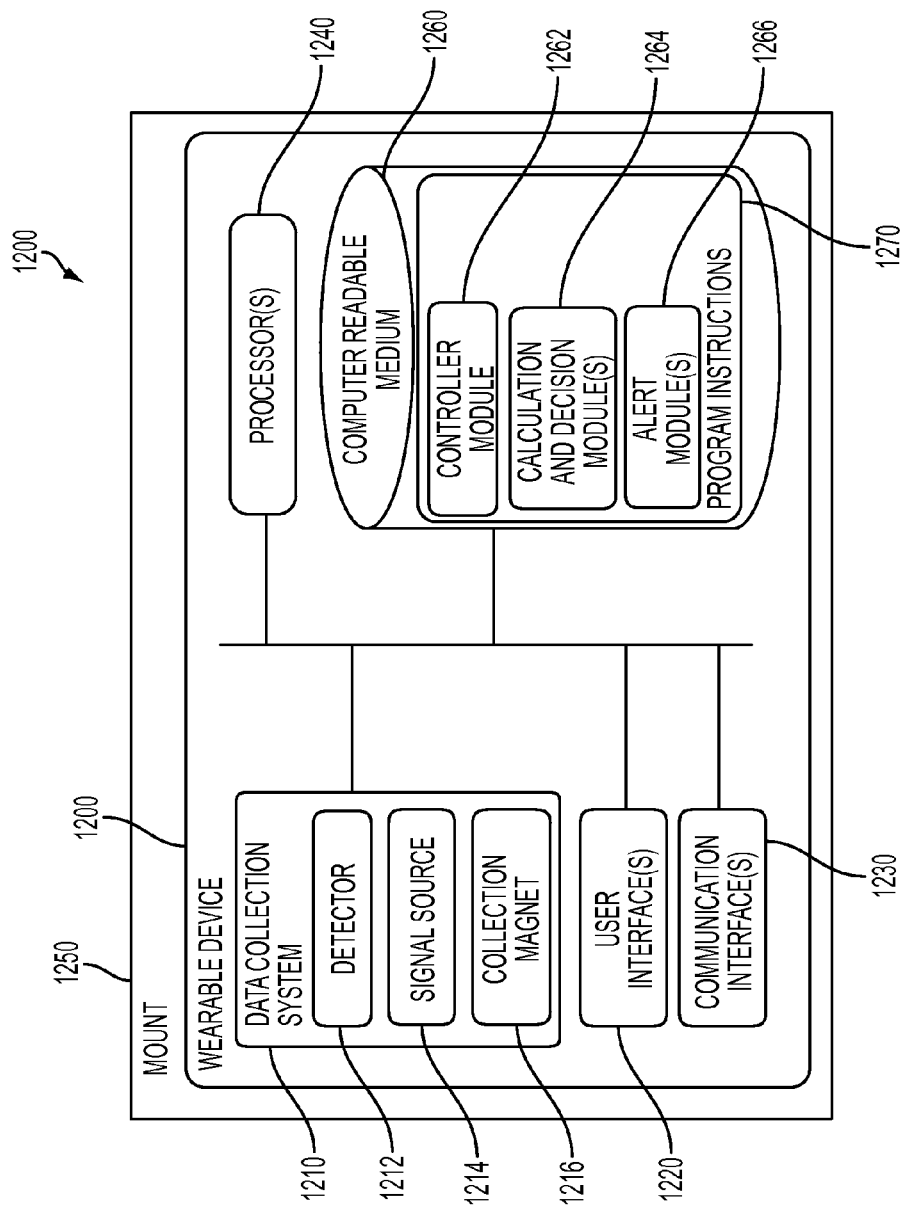
FIG. 12 is a functional block diagram of an example wearable device.

FIG. 12 is a simplified block diagram illustrating the components of a wearable device 1200, according to an example embodiment. Wearable device 1200 is the same as wearable device 1100 in all respects, except that the data collection system 1210 of wearable device 1200 further includes a collection magnet 1216. In this example, the collection magnet 1216 may be used to locally collect magnetic nanoparticles conjugates present in an area of subsurface vasculature proximate to the collection magnet 1216. As described above, collection magnet 1216 is configured to direct a magnetic field into a portion of subsurface vasculature sufficient to cause the magnetic nanoparticles conjugates to collect in a lumen of the portion of subsurface vasculature.

Wearable device 1200 includes a data collection system 1210, which includes a detector 1212, a signal source 1214 (if provided) and a collection magnet 1216, a user interface 1220, a communication interface 1230, a processor 1240 and a computer readable medium 1260 on which program instructions 1270 are stored. All of the components of wearable device 1200 may be provided on a mount 1250. In this example, the program instructions 1270 may include a controller module 1262, a calculation and decision module 1264 and an alert module 1266 which, similar to the example set forth in FIG. 11, include instructions to perform or facilitate some or all of the device functionality described herein. Controller module 1262 further includes instructions for operating collection magnet 1216. For example, controller module 1262 may include instructions for activating collection magnet during a measurement period, for a certain amount of time.

Figure 13:
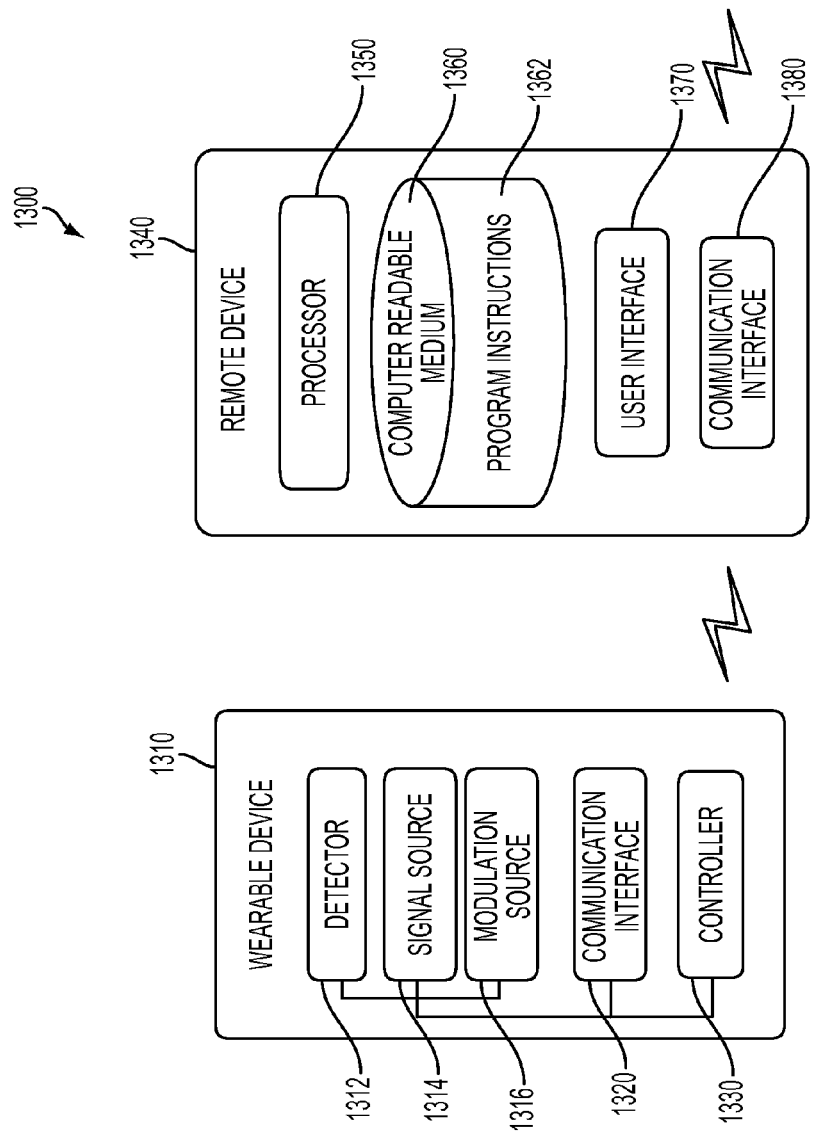
FIG. 13 is a functional block diagram of an example system including a wearable device and a remote device.

FIG. 13 is a simplified block diagram illustrating the components of an example system 1300, including a wearable device 1310. Wearable device 1310 may take the form of or be similar to one of the wrist-mounted devices 500, 600, 700, 800, or 900, shown in FIGS. 5A-B, 6A-6C, 7A-7C, 8, and 9. However, wearable device 1310 may also take other forms, such as an ankle, waist, ear, eye or chest-mounted device. Further, any of devices 500, 600, 700, 800, and 900 may be configured similar to or include any of the components of system 1300, including wearable device 1310.

In particular, FIG. 13 shows an example of a system 1300 including a wearable device 1310 having a detector 1312, in some examples, a signal source 1314, a modulation source 1316, and a communication interface 1320, controlled by a controller 1330. Communication interface 1320 may include an antenna. The components of the wearable device 1310 may be disposed on a mount (not shown) for mounting the device to an external body surface where a portion of subsurface vasculature is readily observable. System 1300 may further include a remote device 1340 in communication with the wearable device 1310, including a processor 1350, a computer readable medium 1360, a user interface 1370, and a communication interface 1380 for communicating with the wearable device 1310 and/or for transmitting data to a server or other remote computing device. While FIG. 13 depicts various components of system 1300 disposed on the wearable device 1310 or the remote device 1340, one of ordinary skill in the art would understand that different configurations and designs are possible, including where all of the components are provided on the wearable device.

Processor 1350 may be a general-purpose processor or a special purpose processor (e.g., digital signal processors, application specific integrated circuits, etc.) and can be configured to execute computer-readable program instructions 1362 that are stored in the computer readable medium 1360 and are executable to provide the functionality of a system 1300 as described herein. The computer readable medium 1360 may include or take the form of one or more non-transitory, computer-readable storage media that can be read or accessed by the processor 1350, and can include volatile and/or non-volatile storage components, such as optical, magnetic, organic or other memory or disc storage, which can be integrated in whole or in part with the processor 1350. The controller 1330 may be configured to operate one or more of the detector 1312, signal source 1314 and modulation source 1316. For example, the controller 1330 may activate the detector 1312, signal source 1314 and modulation source 1316 during each of the pre-set measurement periods.

The program instructions 1362 stored on the computer readable medium 1360 may include instructions to perform or facilitate some or all of the system functionality described herein. For instance, in the illustrated embodiment, program instructions 1362 may include instructions for controller 1330 to operate the detector 1312, signal source 1314 and modulation source 1316. Program instructions 1362 may further cause the processor 1350 to detect the one or more target analytes by differentiating the analyte response signal from the background signal based, at least in part, on a modulation applied by the modulation source 1316. In some cases, the processor may further be configured to differentiate the analyte response signal from the unbound particle signal. Further, the processor 1350 may be configured to determine the concentration of a particular target analyte in the blood from, at least in part, the analyte response signal. The detection and concentration data processed by the processor may be communicated to the patient, for example via the user interface 1370, transmitted to medical or clinical personnel, locally stored or transmitted to a remote server, the cloud, and/or any other system where the data may be stored or accessed at a later time. The program instructions 1362 may also include instructions for operating a user interface 1370, for example, instructions for displaying data transmitted from the wearable device 1310 and analyzed by the processor 1350, or for generating one or more alerts.

VII. Illustrative Methods for Operation of a Wearable Device

Figure 14:
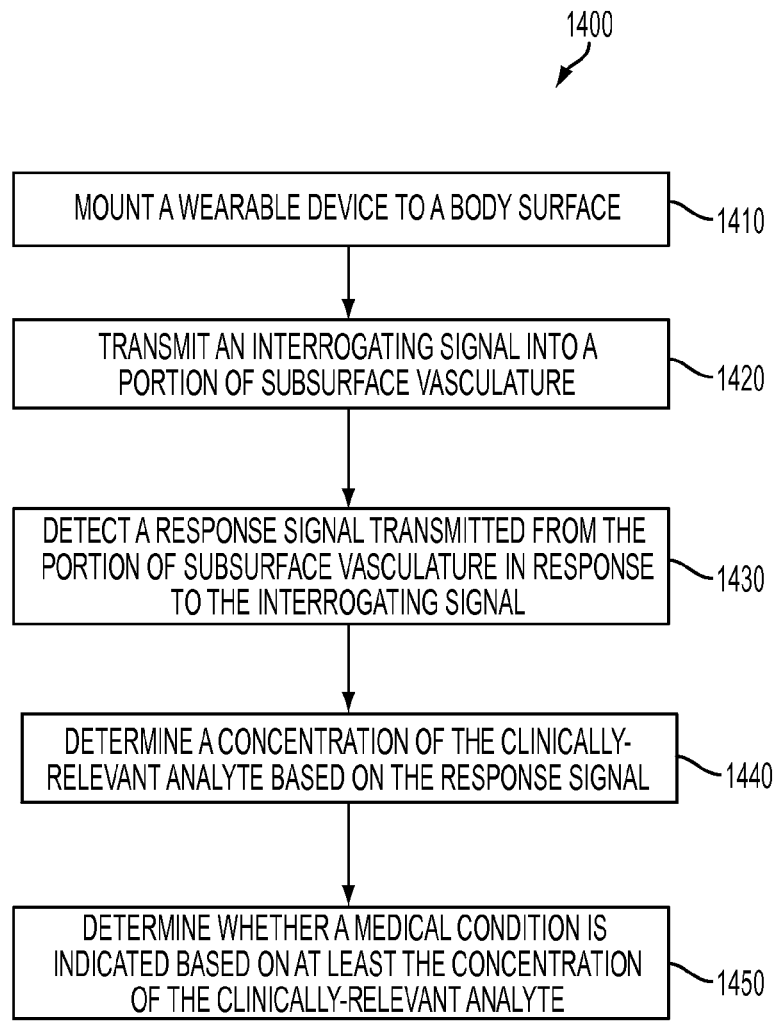
FIG. 14 is a flowchart of an example method for operating a wearable device.

FIG. 14 is a flowchart of a method 1400 for operating a wearable device to take non-invasive, in vivo, real-time measurements of physiological parameters. A wearable device is first mounted to a body surface of a human subject, wherein the body surface is proximate to a portion of subsurface vasculature (1410). In some examples, the wearable device, via a signal source, transmits an interrogating signal into the portion of subsurface vasculature (1420). The wearable device, via a detector, then detects a response signal transmitted from the portion of subsurface vasculature, wherein the response signal is related to binding of a clinically-relevant analyte to nanoparticle conjugates present in a lumen of the subsurface vasculature (1430). In some examples, the response signal is generated in response to an interrogating signal. The nanoparticle conjugates are configured to bind to the clinically-relevant analyte and comprise one or more types of targeting entities such as an antibody or an aptamer. The term "bind" is understood in its broadest sense to also include any detectable interaction between the clinically relevant analyte and the nanoparticle conjugates. The wearable device then determines the presence, absence and/or a concentration of the clinically-relevant analyte based on the response signal (1440) and whether a medical condition is indicated based on at least the presence, absence and/or concentration of the clinically-relevant analyte (1450). Further, in examples where the nanoparticle conjugates are magnetic, the wearable device may further direct a magnetic field into the portion of subsurface vasculature, the magnetic field being sufficient to cause the magnetic nanoparticle conjugates to collect in a lumen of the portion of subsurface vasculature.

Figure 15A:
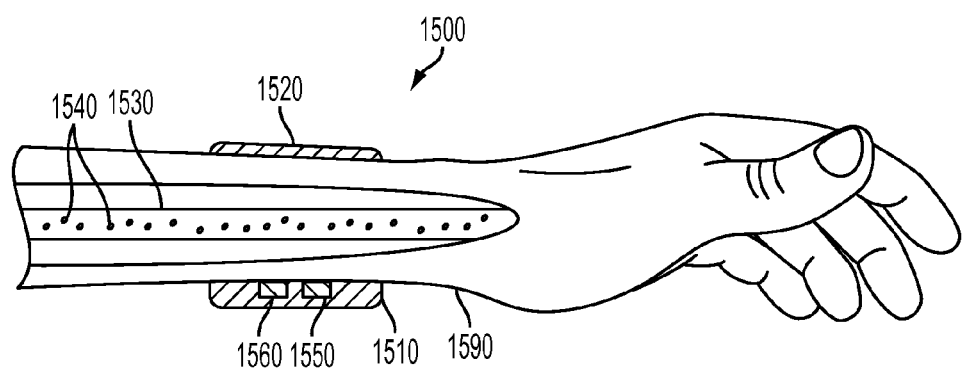
FIG. 15A is side partial cross-sectional view of an example wrist-mounted device, while on a human wrist.
Figure 15B:
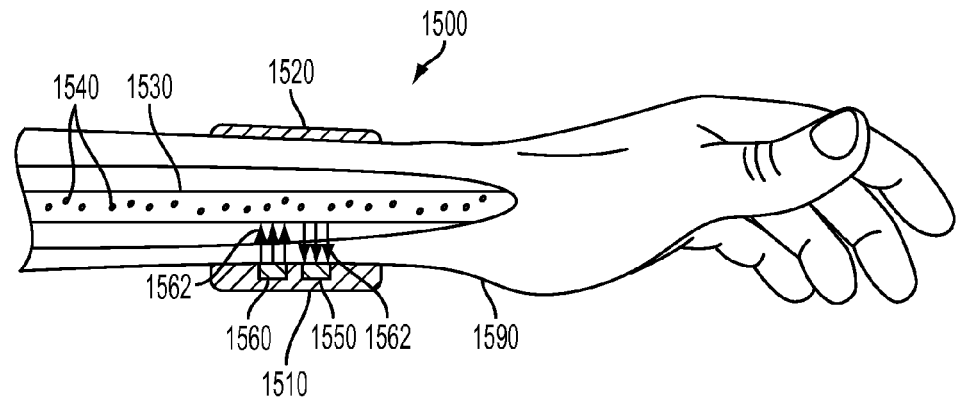
FIG. 15B is side partial cross-sectional view of an example wrist-mounted device, while on a human wrist.

FIGS. 15A-15B, 16A-16B, and 17A-17B are partial cross-sectional side views of a human wrist illustrating the operation of various examples of a wrist-mounted device. In the example shown in FIGS. 15A and 15B, the wrist-mounted device 1500 includes a measurement platform 1510 mounted on a strap or wrist-band 1520 and oriented on the anterior side 1590 of the wearer's wrist. Measurement platform 1510 is positioned over a portion of the wrist where subsurface vasculature 1530 is easily observable. Nanoparticle conjugates 1540 have been introduced into a lumen of the subsurface vasculature by one of the means discussed above. In this example, measurement platform 1510 includes a data collection system having both a detector 1550 and a signal source 1560. FIG. 15A illustrates the state of the subsurface vasculature when measurement device 1500 is inactive. The state of the subsurface vasculature during a measurement period is illustrated in FIG. 15B. At this time, signal source 1560 is transmitting an interrogating signal 1562 into the portion of subsurface vasculature and detector 1350 is receiving a response signal 1552 generated in response to the interrogating signal 1562. The response signal 1552 is related to the binding of a clinically relevant analyte present in the subsurface vasculature to the nanoparticle conjugates 1540. As described above, in some embodiments, an interrogating signal may not be necessary to generate a response signal related to the binding of an analyte to the nanoparticle conjugates.

Figure 16A:
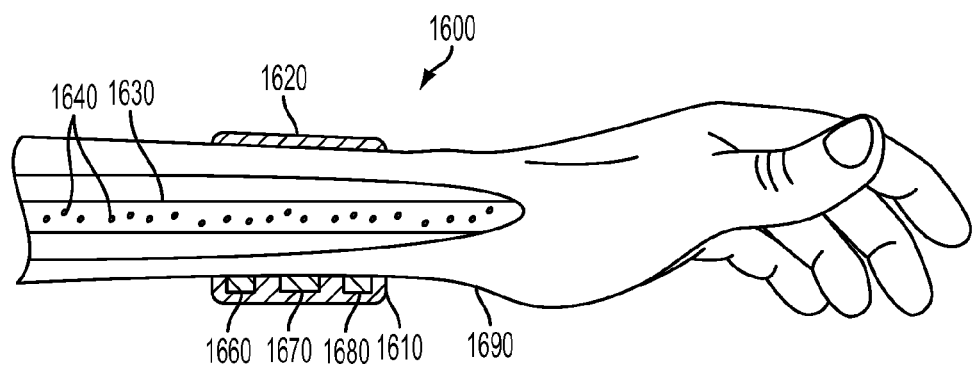
FIG. 16A is side partial cross-sectional view of an example wrist-mounted device, while on a human wrist.
Figure 16B:
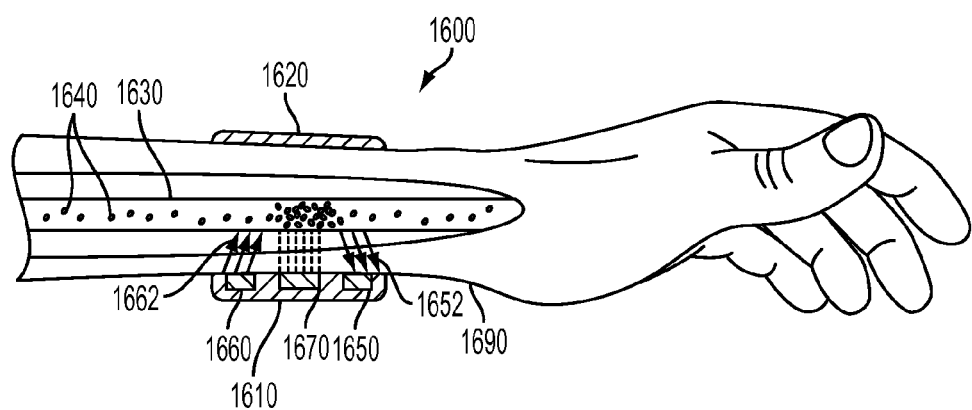
FIG. 16B is side partial cross-sectional view of an example wrist-mounted device, while on a human wrist.

Similar to the system depicted in FIGS. 15A and 15B, FIGS. 16A and 16B illustrate a wrist-mounted device 1600 including a measurement platform 1610 mounted on a strap or wristband 1620 and oriented on the anterior side 1690 of the wearer's wrist. In this example, measurement platform 1610 includes a data collection system having a detector 1650, a signal source 1660 and a collection magnet 1670. FIG. 16A illustrates the state of the subsurface vasculature when measurement device 1600 is inactive. The state of the subsurface vasculature when measurement device 1600 is active during a measurement period is illustrated in FIG. 16B. At this time, collection magnet 1670 generates a magnetic field 1672 sufficient to cause magnetic nanoparticle conjugates 1640 present in a lumen of the subsurface vasculature 1630 to collection in a region proximal to the magnet 1670. Signal source 1660 transmits an interrogating signal 1662 into the portion of subsurface vasculature and detector 1650 is receiving a response signal 1652 generated in response to the interrogating signal 1662. The response signal 1652 is related to the binding of a clinically relevant analyte present in the subsurface vasculature to the magnetic nanoparticle conjugates 1640. As described above, in some embodiments, an interrogating signal may not be necessary to generate a response signal related to the binding of an analyte to the magnetic nanoparticle conjugates.

Figure 17A:
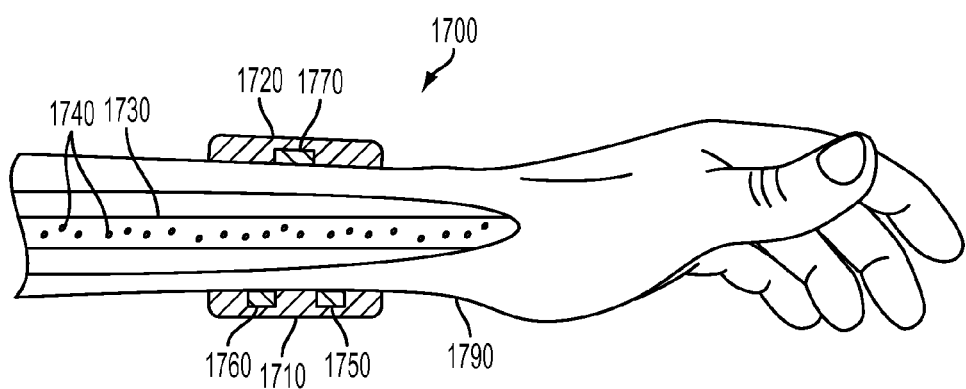
FIG. 17A is side partial cross-sectional view of an example wrist-mounted device, while on a human wrist.
Figure 17B:
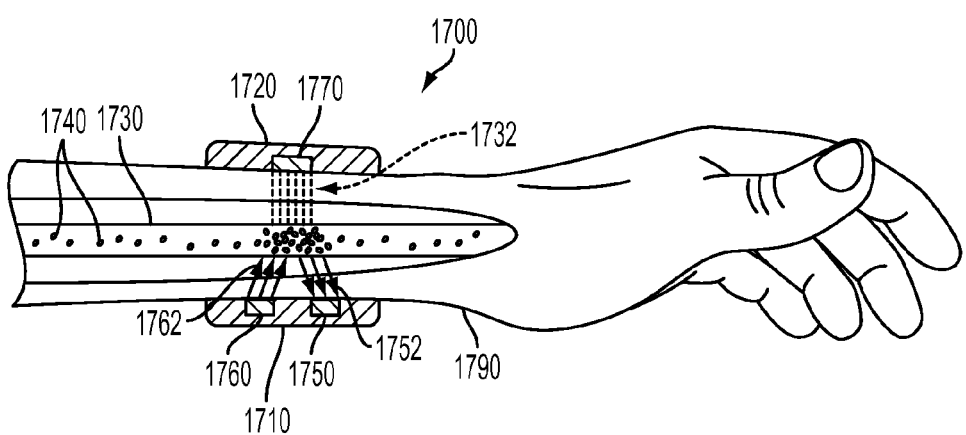
FIG. 17B is side partial cross-sectional view of an example wrist-mounted device, while on a human wrist.

FIGS. 17A and 17B illustrate a further embodiment of a wrist-mounted device 1700 having a measurement platform 1710 disposed on a strap 1720, wherein the detector 1750 and signal source 1760 are positioned on the posterior side 1790 of the wearer's wrist and the collection magnet 1770 is disposed on the anterior side 1780 of the wearer's wrist. Similar to the embodiments discussed above, FIG. 17A illustrates the state of the subsurface vasculature when measurement device 1700 is inactive. The state of the subsurface vasculature when measurement device 1700 is active during a measurement period is illustrated in FIG. 17B. At this time, collection magnet 1770 generates a magnetic field 1732 sufficient to cause magnetic nanoparticle conjugates 1740 present in a lumen of the subsurface vasculature 1730 to collection in a region proximal to the magnet 1770. Signal source 1760 transmits an interrogating signal 1762 into the portion of subsurface vasculature and detector 1750 is receiving a response signal 1752 generated in response to the interrogating signal 1762. The response signal 1752 is related to the binding of a clinically relevant analyte present in the subsurface vasculature to the magnetic nanoparticle conjugates 1740. As described above, in some embodiments, an interrogating signal may not be necessary to generate a response signal related to the binding of an analyte to the magnetic nanoparticle conjugates.

Both FIGS. 16B and 17B illustrate the path of the interrogating signal (1662, 1762) transmitted by the signal source (1660, 1760) and the responsive signal (1652, 1752) detected by the detector (1650, 1750) essentially overlapping over a portion of subsurface vasculature. In some examples, the signal source (1660, 1760) and the detector (1650, 1750) may be angled towards each other so that they are interrogating and detecting from essentially the same area of subsurface vasculature. However, in some instances, such as in the example shown in FIG. 14B, the paths of the interrogating signal (1662, 1762) transmitted by the signal source (1660, 1760) and the responsive signal (1652, 1752) detected by the detector (1650, 1750) may not overlap.

Figure 18:
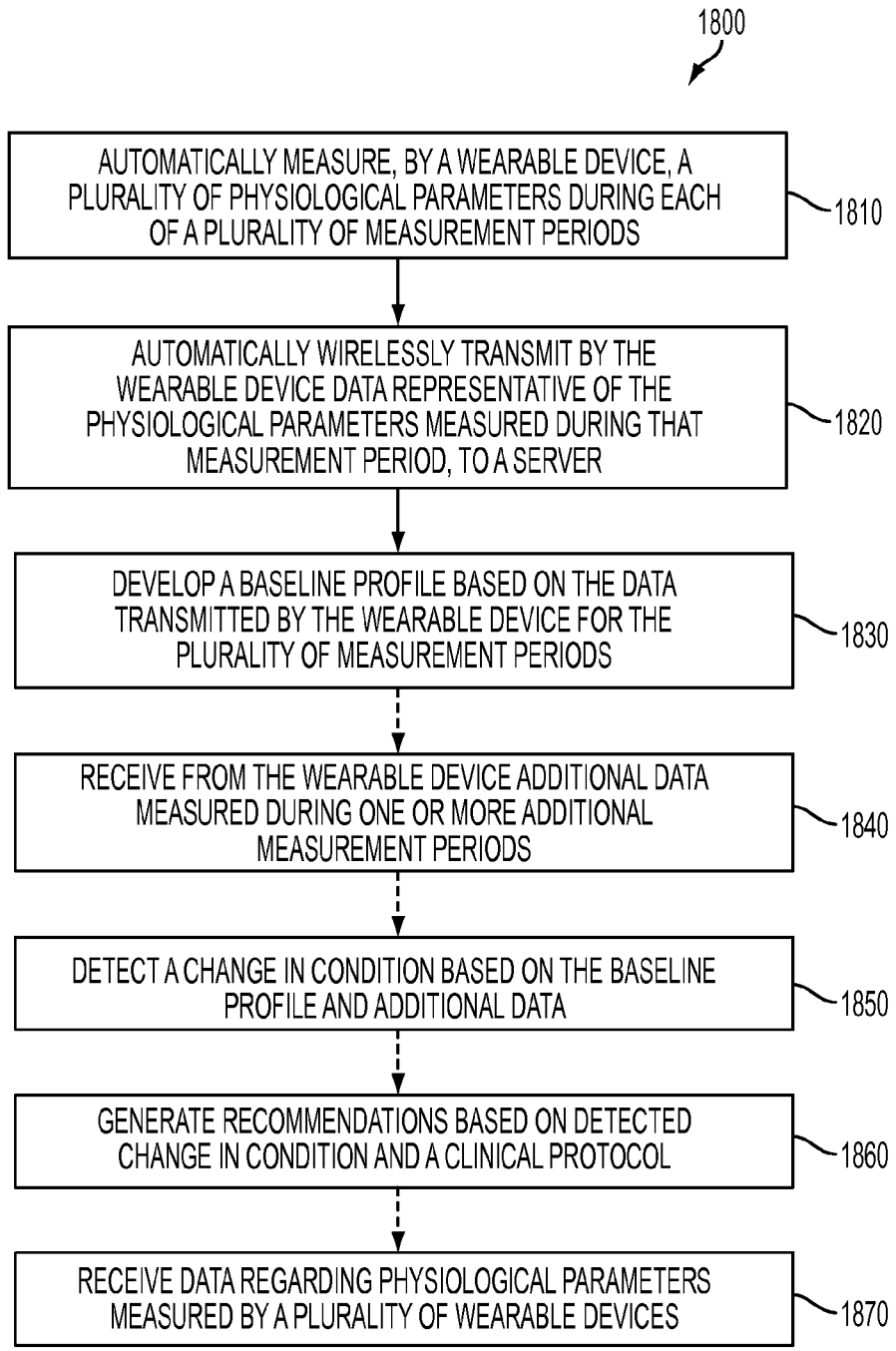
FIG. 18 is a flowchart of an example method for using a wearable device to take real-time, high-density, non-invasive, in vivo measurements of physiological parameters.

VIII. Illustrative methods for Real-Time, High-Density Physiological Data Collection using a Wrist Mounted Device FIG. 18 is a flowchart of a method 1800 for using a wearable device to take real-time, high-density, non-invasive, in vivo measurements of physiological parameters. In a first step, the wearable device automatically measures one or more physiological parameters during each of a plurality of measurement periods (1810). The length of the measurement period may be set on the device itself or may be set remotely, for example, by instruction from a remote server. The device may be configured with many measurement periods each day—for example, continuous, every second, every minute, every hour, every 6 hours, etc.—or may be configured to take measurements once a week or once a month. Further, a different measurement period may be set for each of the physiological parameters being measured. The measurement periods may extend through a plurality of consecutive days and each of the consecutive days may include multiple measurement periods. Each of the consecutive days may further include at least twenty-four measurement periods and the plurality of consecutive days may include at least thirty days. At least some of the physiological parameters are measured by non-invasively detecting one or more analytes in blood circulating in subsurface vasculature proximate to the wearable device.

After conclusion of a measurement period, for each of the plurality of measurement periods, the wearable device transmits to a server data representative of the physiological parameters measured during that measurement period (1820). The wearable device may be configured to automatically transmit the data to a server, may be configured to transmit on command of the wearer, or may be configured to transmit on instruction from a remote server. Further, the device may be configured to automatically transmit the data at the end of each measurement period, or at some more frequent or infrequent rate. For example, the device could be configured to transmit every five minutes, at the end of each day, at the end of the month, at nighttime only, etc.

In response, the server is configured to develop a baseline profile based on the data transmitted by the wearable device for the plurality of measurement periods (1830). In some embodiments, the baseline profile includes an individual baseline profile based on the data transmitted by the wearable device for the plurality of measurement periods for an individual user wearing the wearable device. As described above, the baseline profile may include patterns for how one or more of the wearer's physiological parameters typically change over time, such as during the course of a day, a week, or a month. The baseline profile may further include threshold values of certain target analytes, above or below which a medical condition may be indicated.

After the server has developed an individual baseline profile for a wearer of the device, the server may receive additional data regarding the physiological parameters from the wearable device measured during one or more additional measurement periods (1840). The server may then compare the additional data, collected over additional measurement periods, to the individual baseline profile. If the additional data is consistent with the patterns embodied in the individual baseline profile, the server may determine that the wearer's condition has not changed. On the other hand, if the additional data deviates from the patterns embodied in the baseline profile, the server may detect a change in the wearer's condition (1850). The change in condition could, for example, indicate that the wearer has developed a disease, disorder, or other adverse medical condition or may be at risk for a severe medical condition, such as a stroke or a heart attack, in the near future.

If the server detects a change in condition based on the individual baseline profile and the additional data, it may generate one or more recommendations based on the detected change in condition and a clinical protocol (1860). For example, the server may generate a recommendation that the wearer take a particular medication or supplement, schedule an appointment with a medical professional, go to the hospital to seek immediate medical attention, abstain from certain activities, etc. The server may also be configured to receive data regarding physiological parameters measured by a plurality of wearable devices (1870) and use that data to develop, at least in part, the clinical protocol. The clinical protocol may also be developed based, at least in part, on any known health information or medical history of the wearer, and/or on recognized standards of care in the medical field. The wearable device may receive the one or more recommendations generated by the server (1870) and provide an indication of the one or more recommendations via a user interface on the wearable device.

In some embodiments, the server may be configured to receive data regarding physiological parameters measured by a plurality of wearable devices. The server may use this data collected from a plurality of wearable devices—worn by a plurality of users—to develop, at least in part, a population baseline profile. Such population baseline profiles may be used, for example, for comparison with an individual's baseline profile. Those of skill in the art will readily recognize that comparison of an individual's physiological parameters measured over time to that individual's own baseline may not be sufficient to recognize an abnormality in that physiological parameter. For example, while a physiological parameter for an individual wearer of the device may not deviate from that individual's baseline, that individual baseline may be well above the population baseline generated from data collected from a plurality of wearers of the device. Thus, comparison to what is "normal" or "average" for a population may be necessary for effective identification or prevention of a medical condition in an individual.

Accordingly, the server may further be configured to receive from the wearable device additional data measured during one or more additional measurement periods, detect a change in condition based on the population baseline profile and the additional data, and generate one or more recommendations based on the detected change in condition and a clinical protocol. The wearable device may receive the one or more recommendations generated by the server and provide an indication of the one or more recommendations via a user interface on the wearable device.

Figure 19:
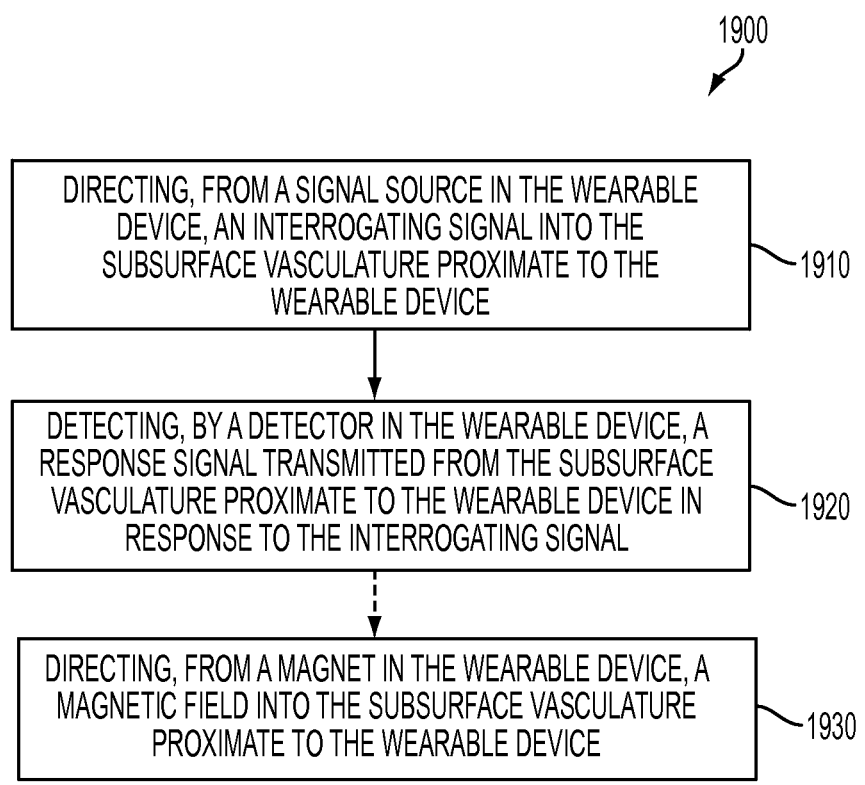
FIG. 19 is a flowchart of an example method for using a wearable device to take real-time, high-density, non-invasive, in vivo measurements of physiological parameters, in particular steps for measuring one or more analytes in blood circulating in subsurface vasculature proximate to the wearable device.

In further embodiments, the method may include introducing nanoparticle conjugates into the blood, wherein the magnetic nanoparticle conjugates are configured to bind to the one or more analytes. As shown in FIG. 19, the wearable device may non-invasively measure one or more analytes in blood circulating in subsurface vasculature proximate to the wearable device by directing, from a signal source in the wearable device, an interrogating signal into the subsurface vasculature proximate to the wearable device (1910). As discussed above, this step may not be necessary in cases where the nanoparticle conjugates generate a response signal related to binding of the one or more analytes without the need for an interrogating signal. In any case, the wearable device may detect, with a detector, a response signal transmitted from the subsurface vasculature proximate to the wearable device in response to the interrogating signal (1920). The response signal is related to binding of the one or more analytes to the nanoparticle conjugates. In examples where an interrogating signal is used, the interrogating signal may include a time-varying magnetic field and the response signal may include an externally-detectable physical motion due to the time-varying magnetic field. The interrogating signal may include an electromagnetic pulse (e.g., a radio frequency (RF) pulse) and the response signal may include a magnetic resonance (MR) signal. The interrogating signal may include electromagnetic radiation having a wavelength between about 400 nanometers and about 1600 nanometers, more particularly, a wavelength between about 500 nanometers and about 1000 nanometers. Where the nanoparticle conjugates also include a fluorophore, the response signal may include fluorescence radiation transmitted by the fluorophore in response to the interrogating signal.

In some examples, the nanoparticle conjugates may also be magnetic. The process of measuring one or more analytes in blood circulating in subsurface vasculature may further include directing, from a magnet in the wearable device, a magnetic field into the subsurface vasculature proximate to the wearable device (1930). The magnetic field is sufficient to cause the magnetic nanoparticle conjugates to collect in a lumen of the subsurface vasculature proximate to the wearable device.

Figure 20:
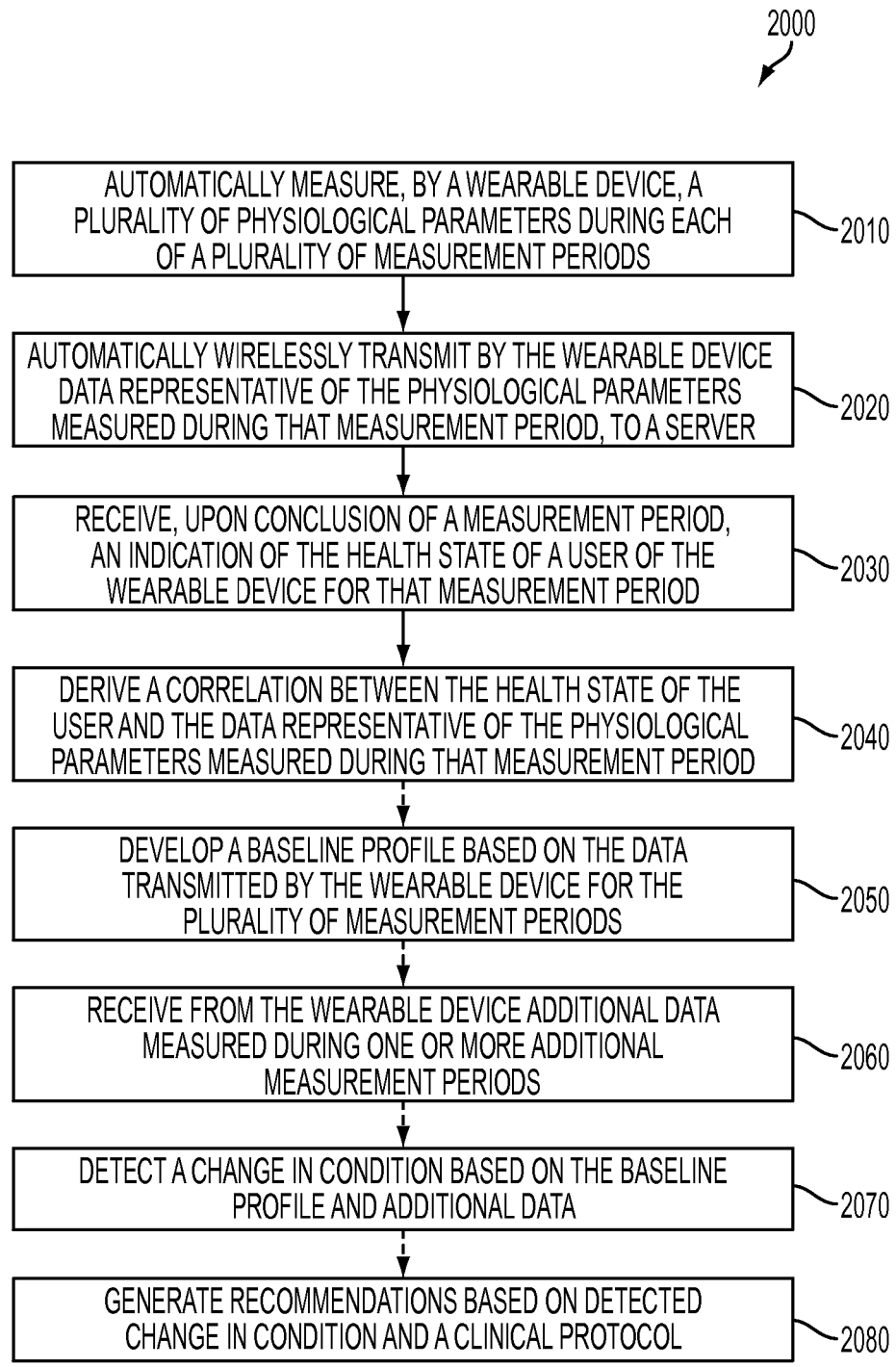
FIG. 20 is a flowchart of an example method for using a wearable device to take real-time, high-density, non-invasive, in vivo measurements of physiological parameters.

FIG. 20 is a flowchart of a method 2000 for using a wearable device to take real-time, high-density, non-invasive, in vivo measurements of physiological parameters. In a first step, the wearable device automatically measures one or more physiological parameters during each of a plurality of measurement periods (2010). The measurement periods may extend through a plurality of consecutive days, wherein each of the consecutive days includes multiple measurement periods. At least some of the physiological parameters are measured by non-invasively detecting one or more analytes in blood circulating in subsurface vasculature proximate to the wearable device.

Upon conclusion of a measurement period for each of the plurality of measurement periods, the wearable device automatically wirelessly transmits to a server data representative of the physiological parameters measured during that measurement period (2020). The server may be configured to receive, upon conclusion of a measurement period, an indication of the health state of a user of the wearable device for that measurement period (2030) and derive a correlation between the health state of the user and the data representative of the physiological parameters measured during that measurement period (2040). For example, the server may be configured to recognize patterns, for example, every time a physiological parameter reaches or drops to a certain level, the wearer of the device indicates that he or she experiences a migraine. Recognition of these patterns or correlations may help medical professionals to recognize, prevent, diagnose and/or treat of health conditions in that individual. Further, the server may be configured to use these correlations to alert the user that a medical condition may be imminent.

A baseline profile may be developed by the server based on the data transmitted by the wearable device for the plurality of measurement periods (2050). The server may further be configured to receive from the wearable device additional data representative of the physiological parameters measured during one or more additional measurement periods (2060), detect a change in condition based on the baseline profile and the additional data (2070), and generate one or more recommendations based on the detected change in condition and a clinical protocol (2080). The clinical protocol may be developed based, at least in part, on the derived correlation. For example, the clinical protocol may indicate that a medical condition may be imminent based on a comparison between current measurement of a physiological parameter and the derived correlation between previously measured physiological parameters and previously reported health state.

In a further example, the server may be configured to receive data regarding physiological parameters measured by a plurality of wearable devices and receive an indication of the health state of the users of the plurality of wearable devices for a plurality of measurement periods. The server may then derive a correlation between the health state of the users and the data representative of the physiological parameters measured during the plurality of measurement periods. Population data of this kind may be significant in that such correlations may never before have been drawn between that physiological parameter and a particular health condition. Such correlations may be used in prediction, prevention, diagnoses and treatment of health conditions. The server may also be configured to receive from the wearable device additional data representative of the physiological parameters measured during one or more additional measurement periods and generate one or more recommendations based on the received additional data and a clinical protocol, wherein the clinical protocol is developed based, at least in part, on the derived correlation.

In a further example, the wearable device itself may be configured to perform the steps described above as being performed by a remote server. For example, the wearable device may be configured to analyze the data representative of the physiological parameters, generate a baseline profile, compare data collected from additional measurement periods to the baseline profile, and generate recommendations based on a clinical protocol. The wearable device may further be configured to transmit, either automatically or on some other frequency, certain data to the remote server.

IX. Conclusion

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

The invention claimed is:

1. A shielded nanoparticle conjugate comprising:
   a nanoparticle;
   at least one targeting entity for binding to tumor cells or tissue in vivo, the at least one targeting entity bound to the nanoparticle; and
   at least one shielding entity for shielding the at least one targeting entity and for unshielding from the at least one targeting entity in a microenvironment of the tumor cells or tissue in vivo, the at least one shielding entity is selected from a protease sensitive bivalent peptide or a bivalent anti-idiotypic aptamer.

2. The shielded nanoparticle conjugate of claim 1, wherein the nanoparticle comprises a polymer material.

3. The shielded nanoparticle conjugate of claim 1, wherein the nanoparticle comprises a non-polymeric material.

4. The shielded nanoparticle conjugate of claim 1, wherein the nanoparticle comprises a magnetic or paramagnetic material.

5. The shielded nanoparticle conjugate of claim 1, wherein the at least one targeting entity comprises an antibody, peptide, protein, nucleic acid, small molecule, carbohydrate, or lipid.

6. The shielded nanoparticle conjugate of claim 1, wherein the bivalent anti-idiotypic aptamer is directed to a tumor metabolite.

7. The shielded nanoparticle conjugate of claim 1, wherein the at least one targeting entity is an antibody and the at least one shielding entity is a protease-sensitive bivalent peptide that binds to the antigen binding site of the antibody.

8. The shielded nanoparticle conjugate of claim 1, wherein the at least one targeting entity is an antibody and the at least one shielding entity is a bivalent anti-idiotypic aptamer with a tumor metabolite-binding domain, wherein the bivalent anti-idiotypic aptamer binds to the antigen binding site of the antibody.

9. The shielded nanoparticle conjugate of claim 1, further comprising at least one detection label.

10. The shielded nanoparticle conjugate of claim 1, further comprising at least one agent to be delivered to the tumor cells.

11. The shielded nanoparticle conjugate of claim 10, wherein the at least one agent comprises at least one anti-tumor agent.

12. The shielded nanoparticle conjugate of claim 10, wherein the at least one agent comprises a contrast imaging agent.

13. The shielded nanoparticle conjugate of claim 1, wherein said shielded nanoparticle conjugate comprises at least one moiety that exhibits fluorescence, luminescence, magnetic or paramagnetic properties.

14. A method for in vivo imaging in a mammal of tumor cells or tissue that express a selected marker; said method comprising the steps of:
   (a) administering to the mammal a composition as recited in claim 1, wherein the at least one targeting entity targets a selected marker of tumor cells or tissue;
   (b) allowing the at least one targeting entity to bind to the selected marker of the tumor cells or tissue in vivo to form a conjugate; and
   (c) imaging the tumor cells or tissue with a non-invasive imaging technique that has a resolution enhanced by a presence of the conjugate on or within the tumor cells or tissue in vivo.

15. The method of claim 14, wherein the non-invasive imaging technique is selected from the group consisting of magnetic resonance imaging (MRI), magnetic spectroscopy, X-ray, positron emission tomography (PET), computer tomography (CT), ultrasonic imaging, and optical imaging.

16. A shielded nanoparticle conjugate comprising:
   a nanoparticle;
   at least one targeting entity for binding to tumor cells or tissue in vivo, the at least one targeting entity bound to the nanoparticle; and
   at least one shielding entity for shielding the at least one targeting entity and for unshielding from the at least one targeting entity in a microenvironment of the tumor cells or tissue in vivo, the at least one shielding entity comprising a pH-sensitive polymer.

17. The shielded nanoparticle conjugate of claim 16, wherein the nanoparticle comprises a polymer material.

18. The shielded nanoparticle conjugate of claim 16, wherein the nanoparticle comprises a non-polymeric material.

19. The shielded nanoparticle conjugate of claim 16, wherein the nanoparticle comprises a magnetic or paramagnetic material.

20. The shielded nanoparticle conjugate of claim 16, wherein the at least one targeting entity comprises an antibody, peptide, protein, nucleic acid, small molecule, carbohydrate, or lipid.

21. The shielded nanoparticle conjugate of claim 16, wherein the at least one targeting entity is an antibody and the at least one shielding entity is a pH-sensitive polymer that degrades in an acidic tumor microenvironment.

22. The shielded nanoparticle conjugate of claim 16, further comprising at least one detection label.

23. The shielded nanoparticle conjugate of claim 16, further comprising at least one agent to be delivered to the tumor cells.

24. The shielded nanoparticle conjugate of claim 23, wherein the at least one agent comprises at least one anti-tumor agent.

25. The shielded nanoparticle conjugate of claim 23, wherein the at least one agent comprises a contrast imaging agent.

26. The shielded nanoparticle conjugate of claim 16, wherein said shielded nanoparticle conjugate comprises at least one moiety that exhibits fluorescence, luminescence, magnetic or paramagnetic properties.

27. A method for in vivo imaging in a mammal of tumor cells or tissue that express a selected marker; said method comprising the steps of:
   (a) administering to the mammal a composition as recited in claim 16, wherein the at least one targeting entity targets a selected marker of tumor cells or tissue;
   (b) allowing the at least one targeting entity to bind to the selected marker of the tumor cells or tissue to form a conjugate; and
   (c) imaging the tumor cells or tissue with a non-invasive imaging technique that has a resolution enhanced by the conjugate present on or within the tumor cells or tissue.

28. The method of claim 27, wherein the non-invasive imaging technique is selected from the group consisting of magnetic resonance imaging (MRI), magnetic spectroscopy, X-ray, positron emission tomography (PET), computer tomography (CT), ultrasonic imaging, and optical imaging.

* * * * *